US006586023B1

(12) United States Patent
Song et al.

(10) Patent No.: US 6,586,023 B1
(45) Date of Patent: *Jul. 1, 2003

(54) PROCESS FOR CONTROLLING RELEASE OF ACTIVE AGENTS FROM A CHEWING GUM COATING AND PRODUCT THEREOF

(75) Inventors: Joo H. Song, Chicago, IL (US); Donald J. Townsend, Moores Hill, IN (US); David W. Record, River Forest, IL (US); Henry T. Tyrpin, Palos Park, IL (US); Michael P. Russell, Evergreen Park, IL (US); Philip G. Schnell, Downers Grove, IL (US); Ronald L. Ream, Plano, IL (US); Christine L. Corriveau, Orland Park, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/552,290

(22) Filed: Apr. 19, 2000

Related U.S. Application Data (63) Continuation of application No. 09/389,211, filed on Sep. 2, 1999, now abandoned, and a continuation-in-part of application No. 09/308,972, filed as application No. PCT/US96/18977 on Nov. 27, 1996.
(60) Provisional application No. 60/112,389, filed on Dec. 15, 1998.

(51) Int. Cl.[7] .............................. A23G 3/30; A61K 9/68
(52) U.S. Cl. .............................. 426/5; 424/48; 424/440
(58) Field of Search .................... 426/3, 5, 6; 424/440, 424/48

(56) References Cited

U.S. PATENT DOCUMENTS

| | | | |
|---|---|---|---|
| 1,298,670 A | 4/1919 | Cramer ......................... 426/3 |
| 1,629,461 A | 5/1927 | Berg et al. | |
| 2,892,753 A | 6/1959 | Schmidt et al. | |
| 2,990,328 A | 6/1961 | Lincoln | |
| 3,011,949 A | 12/1961 | Bilotti ........................... 426/5 |
| 3,029,189 A | 4/1962 | Hardy et al. | |
| 3,047,461 A | 7/1962 | Hardy et al. | |
| 3,075,884 A | 1/1963 | Bilotti et al. ................. 426/5 |
| 3,196,172 A | 7/1965 | Wright, Jr. et al. | |
| 3,308,022 A | 3/1967 | Cummings et al. | |
| 3,498,964 A | 3/1970 | Hayashi | |
| 3,554,767 A | 1/1971 | Daum | |
| 3,590,057 A | 6/1971 | Suzuki et al. | |
| 3,845,217 A | 10/1974 | Ferno et al. | |
| 3,877,468 A | 4/1975 | Lichtneckert et al. | |
| 3,901,248 A | 8/1975 | Lichtneckert et al. | |
| 3,995,064 A | 11/1976 | Ehrgott et al. | |
| 4,154,814 A | 5/1979 | Hand et al. | |
| 4,238,475 A | * 12/1980 | Witzel et al. ............... 426/3 X |
| 4,238,510 A | 12/1980 | Cherukuri et al. | |
| 4,250,195 A | 2/1981 | Cherukuri et al. | |
| 4,283,408 A | 8/1981 | Hirata et al. | |
| 4,317,838 A | 3/1982 | Cherukuri et al. | |
| 4,374,858 A | 2/1983 | Glass et al. | |
| 4,378,374 A | 3/1983 | Reggio et al. | |

(List continued on next page.)

FOREIGN PATENT DOCUMENTS

| | | |
|---|---|---|
| DE | 43 42 568 | 6/1984 |
| EP | 0 202 819 A2 | 11/1986 |
| EP | 0 217 109 A2 | 4/1987 |
| EP | 0 221 850 A2 | 5/1987 |
| EP | 0 239 541 A2 | 9/1987 |
| EP | 0 371 584 A2 | 6/1990 |
| EP | 0 273 809 B1 | 7/1998 |
| FR | 2 345 938 | 10/1977 |
| FR | 2 635 441 | 2/1990 |
| FR | 2 706 771 | 6/1993 |

(List continued on next page.)

OTHER PUBLICATIONS

"Flavor Encapsulation Technologies, Flavor Unit Sweet, Product Management", H&R (undated) ( published at least before Nov. 27, 1996), 25 pages.
Dr. Massimo Calanchi and Dr. Sam Ghanta, "Taste–masking of oral formulations", *Eurand International SpA, Pharmaceutical Manufacturing International*, 1996 (5 pages).
The Eurand Group, Brochure (undated) (published at least before Nov. 27, 1996), (16 pages).
Merck Index, 11th Ed., #1635 "Caffeine" (1989), p. 248.
Merck Index, 12th Ed., #2337 "Cimetidine" (1996), p. 383.
Merck Index, 12th Ed., #3264 "Dimethicone" (1996), p. 544.
Merck Index, 12th Ed., #3972 "Famotidine" (1996), p. 667.
Merck Index, 12th Ed., #6758 "Nizatidine" (1996), p. 1143.
Merck Index, 12th Ed., #6977 "Omeprazole" (1996), p. 1174.
Merck Index, 12th Ed., #8272 "Rabeprazole" (1996), p. 1392.
Merck Index, 12th Ed., #8286 "Ranitidine" (1996), p. 1395.
Product package "CHOOZ Antacid/Calcium Supplement with Calcium Carbonate" distributed by Heritage Consumer Products Co.

(List continued on next page.)

*Primary Examiner*—Arthur L. Corbin
(74) *Attorney, Agent, or Firm*—Steven P. Shurtz; Brinks Hofer Gilson & Lione (57) ABSTRACT

A method for producing a coated chewing gum with a controlled release of an active agent, as well as the chewing gum so produced, is obtained by physically modifying an active agent's properties by coating and drying. An active agent is coated by encapsulation, partially coated by agglomeration, entrapped by absorption, or treated by multiple steps of encapsulation, agglomeration, and absorption. The coated active agent is then co-dried and particle sized to produce a release-modified active agent. When incorporated into a chewing gum coating, these particles release into the mouth but mask bitter and other off-tastes in the mouth, and are readily ingested.

34 Claims, 1 Drawing Sheet

U.S. PATENT DOCUMENTS

| | | | |
|---|---|---|---|
| 4,386,063 A | 5/1983 | Boden | |
| 4,386,106 A | 5/1983 | Merrit et al. | |
| 4,400,372 A | 8/1983 | Muhker et al. | |
| 4,446,135 A | 5/1984 | Fountaine | |
| 4,452,821 A * | 6/1984 | Gergely | 426/5 |
| 4,459,311 A | 7/1984 | DeTora et al. | |
| 4,474,749 A | 10/1984 | Kruppa | |
| 4,512,968 A | 4/1985 | Komiyama et al. | |
| 4,533,556 A | 8/1985 | Piccolo et al. | |
| 4,555,407 A | 11/1985 | Kramer et al. | |
| 4,563,345 A | 1/1986 | Arrick | |
| 4,639,368 A | 1/1987 | Niazi et al. | 424/48 |
| 4,647,450 A | 3/1987 | Peters et al. | |
| 4,711,774 A | 12/1987 | Denick, Jr. et al. | |
| 4,716,033 A | 12/1987 | Denick, Jr. | |
| 4,737,366 A | 4/1988 | Gergely et al. | |
| 4,753,800 A | 6/1988 | Mozda | |
| 4,753,805 A * | 6/1988 | Cherukuri et al. | 426/5 |
| 4,755,389 A | 7/1988 | Jones et al. | |
| 4,758,424 A | 7/1988 | Denick, Jr. et al. | |
| 4,822,597 A | 4/1989 | Faust et al. | |
| 4,822,816 A | 4/1989 | Markham | |
| 4,828,820 A | 5/1989 | Glass et al. | |
| 4,832,994 A | 5/1989 | Fey | |
| 4,835,162 A | 5/1989 | Abood | |
| 4,849,227 A | 7/1989 | Cho | |
| 4,853,212 A | 8/1989 | Faust et al. | |
| 4,867,989 A | 9/1989 | Silva et al. | |
| 4,882,152 A | 11/1989 | Yang et al. | |
| 4,894,234 A | 1/1990 | Sharma et al. | |
| 4,908,211 A | 3/1990 | Paz | |
| 4,908,212 A | 3/1990 | Kwon et al. | |
| 4,929,447 A | 5/1990 | Yang | |
| 4,929,508 A | 5/1990 | Sharma et al. | |
| 4,933,184 A | 6/1990 | Tsuk | |
| 4,935,242 A | 6/1990 | Sharma et al. | |
| 4,938,963 A | 7/1990 | Parnell | |
| 4,944,949 A | 7/1990 | Story et al. | |
| 4,963,369 A | 10/1990 | Song et al. | |
| 4,968,511 A | 11/1990 | D'Amelia et al. | |
| 4,968,716 A | 11/1990 | Markham | |
| 4,971,079 A | 11/1990 | Talapin et al. | |
| 4,971,787 A | 11/1990 | Cherukuri et al. | 426/3 |
| 4,975,270 A | 12/1990 | Kehoe | |
| 4,978,537 A * | 12/1990 | Song | 426/5 |
| 4,997,659 A * | 3/1991 | Yatka et al. | 426/3 |
| 5,013,716 A * | 5/1991 | Cherukuri et al. | 426/3 X |
| 5,015,464 A | 5/1991 | Strobridge | |
| 5,045,325 A | 9/1991 | Lesko et al. | |
| 5,070,085 A | 12/1991 | Markham | |
| 5,110,608 A | 5/1992 | Cherukuri | |
| 5,124,156 A | 6/1992 | Shibata et al. | |
| 5,126,151 A | 6/1992 | Bodor et al. | |
| 5,139,787 A | 8/1992 | Broderick et al. | |
| 5,154,927 A | 10/1992 | Song et al. | |
| 5,156,842 A | 10/1992 | Mulligan | |
| 5,179,122 A | 1/1993 | Greene et al. | |
| 5,182,099 A | 1/1993 | Jonsson et al. | |
| 5,229,137 A | 7/1993 | Wolfe | |
| 5,244,670 A | 9/1993 | Upson et al. | |
| 5,284,657 A | 2/1994 | Lu et al. | |
| 5,286,500 A | 2/1994 | Synosky et al. | |
| 5,294,433 A | 3/1994 | Singer et al. | |
| 5,294,449 A | 3/1994 | Greenberg | |
| 5,340,566 A | 8/1994 | Curtis et al. | |
| 5,378,131 A | 1/1995 | Greenberg | |
| 5,380,530 A | 1/1995 | Hill | |
| 5,380,535 A | 1/1995 | Geyer et al. | |
| 5,397,580 A | 3/1995 | Song et al. | |
| 5,410,028 A | 4/1995 | Asami et al. | |
| 5,419,919 A | 5/1995 | Song et al. | |
| 5,433,960 A | 7/1995 | Meyers | 426/5 |
| 5,445,834 A | 8/1995 | Burger et al. | |
| 5,455,286 A | 10/1995 | Amidon et al. | |
| 5,456,677 A | 10/1995 | Spector | |
| 5,487,902 A * | 1/1996 | Andersen et al. | 426/3 |
| 5,488,962 A | 2/1996 | Perfetti | |
| 5,494,685 A | 2/1996 | Tyrpin et al. | |
| 5,496,541 A | 3/1996 | Cutler | |
| 5,512,306 A | 4/1996 | Carlsson et al. | |
| 5,523,097 A | 6/1996 | Song et al. | |
| 5,534,272 A | 7/1996 | Bernstein | |
| 5,543,160 A | 8/1996 | Song et al. | |
| 5,554,380 A | 9/1996 | Cuca et al. | |
| 5,569,477 A | 10/1996 | Nesbitt | |
| 5,571,528 A | 11/1996 | Lee et al. | |
| 5,571,543 A | 11/1996 | Song et al. | |
| 5,576,344 A | 11/1996 | Sandler et al. | |
| 5,580,590 A | 12/1996 | Hartman | |
| 5,582,855 A | 12/1996 | Cherukuri et al. | |
| 5,585,110 A | 12/1996 | Kalili et al. | |
| 5,593,685 A | 1/1997 | Bye et al. | |
| 5,601,858 A | 2/1997 | Manshukhani | |
| 5,605,698 A | 2/1997 | Ueno | |
| 5,607,697 A | 3/1997 | Alkire et al. | |
| 5,618,517 A | 4/1997 | Miskewitz | |
| 5,628,986 A | 5/1997 | Sanker et al. | |
| 5,629,013 A | 5/1997 | Upson et al. | |
| 5,629,026 A | 5/1997 | Davis | |
| 5,629,035 A | 5/1997 | Miskewitz | |
| 5,645,853 A | 7/1997 | Winston et al. | |
| 5,651,987 A | 7/1997 | Fuisz | |
| 5,656,652 A | 8/1997 | Davis | |
| 5,665,386 A | 9/1997 | Bebet et al. | |
| 5,667,802 A | 9/1997 | Grimberg | |
| 5,693,334 A | 12/1997 | Miskewitz | |
| 5,698,215 A | 12/1997 | Kalili et al. | |
| 5,702,687 A | 12/1997 | Miskewitz | |
| 5,711,961 A | 1/1998 | Reiner et al. | |
| 5,716,928 A | 2/1998 | Benet et al. | |
| 5,736,175 A | 4/1998 | Cea et al. | |
| 5,744,164 A | 4/1998 | Chauffard et al. | |
| 5,753,255 A | 5/1998 | Chavkin et al. | |
| 5,756,074 A | 5/1998 | Ascione et al. | |
| 5,800,847 A | 9/1998 | Song et al. | |
| 5,824,291 A | 10/1998 | Howard | |
| 5,834,002 A | 11/1998 | Athanikar | |
| 5,846,557 A | 12/1998 | Eisenstadt et al. | 424/439 |
| 5,854,267 A | 12/1998 | Berlin et al. | |
| 5,858,383 A | 1/1999 | Precopio | |
| 5,858,412 A | 1/1999 | Staniforth et al. | |
| 5,858,413 A | 1/1999 | Jettka et al. | |
| 5,858,423 A | 1/1999 | Yajima et al. | |
| 5,866,179 A | 2/1999 | Testa | |
| 5,877,173 A | 3/1999 | Olney et al. | |
| 5,882,702 A | 3/1999 | Abdel-Malik et al. | |
| 5,889,028 A | 3/1999 | Sandborn et al. | |
| 5,889,029 A | 3/1999 | Rolf | |
| 5,897,891 A | 4/1999 | Godfrey | |
| 5,900,230 A | 5/1999 | Cutler | |
| 5,912,007 A | 6/1999 | Pan et al. | |
| 5,912,030 A | 6/1999 | Huziinec et al. | |
| 5,916,606 A | 6/1999 | Record et al. | |
| 5,922,346 A | 7/1999 | Hersh | |
| 5,922,347 A | 7/1999 | Häusler et al. | |
| 5,928,664 A | 7/1999 | Yang et al. | |
| 5,958,380 A | 9/1999 | Winston et al. | |
| 5,958,472 A | 9/1999 | Robinson et al. | |
| 5,980,955 A | 11/1999 | Grennberg et al. | |
| 5,989,588 A | 11/1999 | Korn et al. | |
| 6,024,988 A | 2/2000 | Ream et al. | 426/3 |

| | | | |
|---|---|---|---|
| 6,066,342 A | 5/2000 | Gurol et al. | |
| 6,077,524 A | 6/2000 | Bolder et al. | |
| 6,090,412 A | 7/2000 | Hashimoto et al. | |
| 6,165,516 A | 12/2000 | Gudas et al. | |

FOREIGN PATENT DOCUMENTS

| | | | |
|---|---|---|---|
| GB | 0 934 596 | | 8/1963 |
| GB | 0 963 518 | | 7/1964 |
| GB | 1 489 832 | | 10/1977 |
| GB | 2181646 A | | 4/1987 |
| IT | 02173487 | | 7/1997 |
| JP | 86/242561 | | 10/1986 |
| JP | 91-112450 | | 5/1991 |
| JP | 91-251533 | | 11/1991 |
| JP | 94-303911 | | 11/1994 |
| JP | 96-19370 | | 1/1996 |
| KR | 94-2868 | | 4/1994 |
| WO | WO 84/02271 | | 6/1984 |
| WO | WO 90/12511 | | 11/1990 |
| WO | WO 90/12583 | | 11/1990 |
| WO | WO 92/06680 | | 4/1992 |
| WO | WO 95/00038 | | 1/1995 |
| WO | WO 95/00039 | | 1/1995 |
| WO | WO 95/10290 | | 4/1995 |
| WO | WO 96/00070 | | 1/1996 |
| WO | WO 96/03975 | | 2/1996 |
| WO | WO 97/21424 | | 6/1997 |
| WO | WO 97/24036 | | 6/1997 |
| WO | 98/23165 | * 6/1998 | .................. 426/5 |
| WO | WO 98/23166 | | 6/1998 |
| WO | WO 98/23167 | | 6/1998 |
| WO | WO 99/33352 | | 7/1999 |
| WO | WO 99/44436 | | 9/1999 |
| WO | WO 00/13523 | | 3/2000 |
| WO | WO 00/35296 | | 6/2000 |
| WO | WO 00/35298 | | 6/2000 |
| WO | WO 00/38532 | | 7/2000 |

OTHER PUBLICATIONS

Hertiage Consumer Products Co. article from the Internet "Cosmetics and Toiletries, The Heritage Story", printed Jul. 20, 2000, <http://www.cnewsusa.com/Connecticut/14997.html>, 1 page.

The United States Pharmacopeia The National Formulary—"General Information", dated Jan. 1, 1990 pp 1624–1625 and pp 1696–1697.

Gumtech article from the Internet "Customized Solutions For Customer Brands", printed Oct. 18, 2000, <http://www.gum–tech.com/cus–brands.html>, 3 pages.

Product package for Stay Alert Caffeine Supplement Gum, distributed by Amurol Confections Company (first quarter 1998).

Rabeprazole article from the Internet "Rabeprazole: Pharmacokinetics and Safety in the Elderly", printed Sep. 22, 2000, <http://www.mmhc.com/cg/articles/CG9905/Hum–phries.html>, 2 pages.

Brochure for "Minerals Technologies Specialty Minerals", 1998, 19 pages.

Akitoshi et al., Abstract "Acceleration of Transdermal Absorption of Pharmaceuticals by Essential Oils and Organic Solvents," Chem. Abst., 112:125228t, 1990.

Bradford, A Rapid and Sensitive Method for the Quantification of Microgram Quantities of Protein Utilizing the Principle of Protein–Dye Binding, Analytical Biochemistry, 72:248–254 (1976).

Nielsen et al., P–Glycoprotein as Multidrug Transporter: A Critical Review of Current Multidrug Resistant Cell Lines, Chimica et Biophysica Acta., 1139:169–183 (1992).

Adams, M.W., d–Alpha Tocopheryl Polyethylene glycol 1000 Succinate (Eastman vitamin E TPGS) as an Emulsifier and Bioenhancer for Drugs and Lipophilic Compounds, 6th International Conference on Pharmaceutical Technology, Paris, Jun. 2–4, 1992.

Chang, Tammy et al., "The Effect of Water–Soluble Vitamin E on Cyclosporine Pharmacokinetics in Healthy Volunteers," Abstract in American Society to Clinical Pharmacology and Therapeutics, 57(2):163, Feb. 1995.

Hebert, Mary F. et al.; "Bioavailability of Cyclosporine with Concomitant Rifampin Administration is Markedly Less Than Predicted by Hepatic Enzyme Induction" (1992) *Clin. Pharmacol. Ther.* 52:453–457.

Kronbach, Thomas et al.; "Oxidation of Midazolam and Triazolam by Human Liver Cytochrome P450IIIA4" (1989) *Molec. Pharm.* 36:89–96.

Lalka et al.; "The Hepatic First–Pass Metabolism of Problematic Drugs" (1993) *J. Clin. Pharmacol.* 33:657–669.

Lum et al.; "Clinical Trials of Modulation of Multidrug Resistance. Pharmacokinetic and Pharmacodynamic Considerations" (1993) *Cancer* 72:3502–3514.

Muranishi, Shozo; "Absorption Enhancers" (1990) *Crit. Rev. Ther. Drug Carrier Sys.*, 7:1–33.

Somberg et al.; "The Clinical Implications of First–Pass Metabolism: Treatment Strategies for the 1990's" (1993) *J. Clin. Pharmacol.* 33:670–673.

Tam, Yun K.; "Individual Variation in First–Pass Metabolism" (1993) *Clin. Pharmacokinet.* 25:300–328.

Van Hoogdalem et al.; "Intestinal Drug Absorption Enhancement: An Overview" (1989) *Pharmacol. Ther.* 44:407–443.

Warren et al.; "Increased Accumulation of Drugs in Multidrug–Resistant Cell Induced by Liposomes" (1992) *Cancer Research* 52:3241–3245.

Watkins, Paul B.; "The Role of Cytochromes P–450 in Cyclosporine Metabolism" (1990) *J. Am. Acad. Dermacol.* 23:1301–1309.

Wrighton et al.; "In Vitro Methods for Assessing Human Hepatic Drug Metabolism: Their Use in Drug Development" (1993) 25:453–484.

Wu et al.; "Use of IV and Oral Drug Levels from Cyclosporene (CsA) with Concomitant Rifampin to Differentiate Gut Absorption and Metabolism" (1993) *Pharm. Res.* 10:abstract ppdm8185.

Zamora et al.; "Physical–Chemical Properties Shared by Compounds that Modulate Multidrug Resistance in Human Loukemic Cells" (1988) *Molec. Pharmacol.* 33:454–462.

U.A. patent application Ser. No. 09/286/818, filed Apr. 6, 1999.

U.S. patent application Ser. No. 09/421,905, filed Oct. 20, 1999.

U.S. patent application Ser. No. 09/510,878, filed Feb. 23, 2000.

U.S. patent application Ser. No. 09/535,458, filed Mar. 24, 2000.

U.S. patent application Ser. No. 09/591,256, filed Jun. 9, 2000.

U.S. patent application Ser. No. 09/618,808, filed Jul. 18, 2000.

U.S. patent application Ser. No. 09/621,643, filed Jul. 21, 2000.

U.S. patent application Ser. No. 09/621,780, filed Jul. 21, 2000.
U.S. patent application Ser. No. 09/631,326, filed Aug. 3, 2000.
U.S. patent application Ser. No. 09/651,514, filed Aug. 30, 2000.
U.S. patent application Ser. No. 09/654,464, filed Sep. 1, 2000.
U.S. patent application Ser. No. 09/653,669, filed Sep. 1, 2000.
U.S. patent application Ser. No. 09/671,552, filed Sep. 27, 2000.
U.S. patent application Ser. No. 09/714,571, filed Nov. 16, 2000.
U.S. patent application Ser. No. 09/748,699, filed Dec. 22, 2000.
U.S. patent application Ser. No. 09/747,323, filed Dec. 22, 2000.
U.S. patent application Ser. No. 09/747,300, filed Dec. 22, 2000.
U.S. patent application Ser. No. 09/749,983, filed Dec. 27, 2000.
U.S. patent application Ser. No. 09/759,561, filed Jan. 11, 2001.
U.S. patent application Ser. No. 09/759,838, filed Jan. 11, 2001.

James G. Elliott, "Application of Antioxidant Vitamins in Foods and Beverages" *Food Technology*, (Feb., 1999), pp. 46–48.

C. Curtis Vreeland, "Nutraceuticals Fuel Confectionery Growth" *Candy R&D*, (Mar., 1999), pp. 29, 31–32, 34–35.

Kitty Broihier, R.D., "Foods of Tomorrow, Milking The Nutrition Market", *Food Processing*, (Mar., 1999), pp. 41, 42 and 44.

Kitty Broihier, R.D., "Tea Time For Nutraceuticals, New Black, Green Tea Products Brew Up a Bevy Of Health Benefits", *Food Processing*; (Mar., 1999), pp. 59, 61 and 63.

Andrea Allen, Jack Neff, Lori Dahm and Mary Ellen Kuhn, "Exclusive Guide to Wellness Foods and Nutraceuticals", Food Processing (Special Supplement), (Mar., 1999).

Product package "Aspergum" distributed by Heritage Consumer Products, LLC (on sale prior to Nov. 27, 1995).

Product package "Chew & Sooth Zinc Dietary Supplement Gum" by Gumtech International, Inc. (undated).

Product package "Dental Care the Baking Soda Gum" distributed by Church & Dwight Co., Inc. (1998).

Product package "BreathAsure Dental Gum" by Breath Asure, Inc. (1998).

Product package "Trident Advantage with Baking Soda" distributed by Warner–Lambert Co. (1998).

* cited by examiner

PROCESS FOR CONTROLLING RELEASE OF ACTIVE AGENTS FROM A CHEWING GUM COATING AND PRODUCT THEREOF

REFERENCE TO EARLIER FILED APPLICATIONS

The present application is a continuation of application Ser. No. 09/389,211, filed Sep. 2, 1999, abandoned which in turn claims the benefit of the filing date under 35 U.S.C. §119(e) of U.S. Provisional Application Serial No. 60/112, 389, filed Dec. 15, 1998. The entire text of the referenced applications are incorporated herein by reference without prejudice or disclaimer. This application is also a continuation-in-part of application Ser. No. 09/308,972, filed May 27, 1999, now U.S. Pat. No. 6,165,516, nationalization of PCT/US96/18977, filed Nov. 27, 1996, designating the Unitet State.

BACKGROUND OF THE INVENTION

The present invention relates to methods for producing chewing gum. More particularly the invention relates to producing chewing gum containing an effective amount of an active ingredient or ingredients, including a stimulant known as caffeine. The caffeine or other active ingredient that is added to the chewing gum has been treated to control its rate of release from chewing gum by adding the treated active agent to a gum coating.

In recent years, efforts have been devoted to controlling release characteristics of various ingredients in chewing gum. Most notably, attempts have been made to delay the release of sweeteners and flavors in various chewing gum formulations to thereby lengthen the satisfactory chewing time of the gum. Delaying the release of sweeteners and flavors can also avoid an undesirable overpowering burst of sweetness or flavor during the initial chewing period. On the other hand, some ingredients have been treated so as to increase their rate of release in chewing gum.

Besides sweeteners, other ingredients may require a controlled release from chewing gum. In certain embodiments, it is contemplated that the active agent that is added to the gum may be a stimulant such as caffeine. However, stimulants are not generally released very readily. An active stimulant such as caffeine may be encapsulated in a water soluble matrix such that, during the chewing period, the caffeine may be released quickly, resulting in a fast release of stimulant as in a beverage. This would allow chewing gum to be a carrier for an active agent such as caffeine and, with these fast release characteristics the gum may be used as an effective stimulant.

In some instances, serious taste problems may arise because of the bitter nature of many active agents. A prolonged or delayed release of an active agent(s) would allow for the use of the active agent(s) in gum, but the low level of release of such an agent may keep the level of that agent below the taste threshold of the active agent, and not give chewing gum a bitter taste quality. In addition, active agents may also have other unpleasant tastes that may be overcome by reducing the release rate of active agent from a chewing gum.

Another aspect of the present invention contemplates the use of encapsulation techniques. For example, it may be that active agents may also be unstable in a chewing gum environment. In such cases, various methods of encapsulation may be needed to improve stability of the active agent. In other circumstances, active agents may not be readily released from the chewing gum matrix and their effect may be considerably reduced. In such a situation, a fast release encapsulation may be needed to release active agent(s) from the gum matrix.

Other methods contemplated are method of controlling release of active agent(s) from gum. These methods would be useful in not releasing the active agent in the oral cavity during gum chewing, but allowing the active agent to be ingested during chewing. This will keep the active agent from becoming effective until after it enters the digestive track.

Thus, there are specific advantages to adding active agent(s) to chewing gum by controlled release mechanisms.

The use of caffeine in chewing gum is disclosed in U.S. Pat. No. 1,298,670. The controlled release of caffeine in chewing gum is disclosed in PCT Patent Publication No. WO 98/23165.

Chewing gum containing caffeine as a stimulant and to combat fatigue and migraine headaches is disclosed in French Patent No. 2 345 938 and in West Germany Patent No. 43 42 568.

Also, two Japanese Patent Publications, Nos. JP 1991-112450 and JP 1991-251533, disclose the use of caffeine in chewing gum to reduce drowsiness.

In Japanese Patent Publication No. JP 1996-019370, caffeine is added to chewing gum as an after meal chewing gum to replace tooth brushing.

Caffeine is a well known stimulant from coffee and tea, and several patents disclose the use of coffee or tea in gum, such as Japanese Patent Publication No. JP 1994-303911, South Korea Patent Publication No. 94-002868, and PCT Patent Publication No. WO 95/00038.

SUMMARY OF THE INVENTION

The present invention provides a method of producing chewing gum with physically modified active agents such as caffeine to control their release. Such active agents are added to a gum coating to deliver the active agents systemically without unpleasant tastes. The present invention also relates to the chewing gum so produced. Physically modified active agents such as caffeine may be added to sucrose-type gum formulations and sucrose-type coatings. The formulation may be a low or high moisture formulation containing low or high amounts of moisture containing syrup. Physically modified active agents such as caffeine may also be used in low or non-sugar gum formulations and coatings that use sorbitol, mannitol, other polyols or carbohydrates. Non-sugar formulations may include low or high moisture sugar-free chewing gums.

Active agents such as caffeine and the other active agents described herein may be combined or co-dried with bulk sweeteners typically used in chewing gum before the active agent(s) are physically modified. Such bulk sweeteners are sucrose, dextrose, fructose and maltodextrins, as well as sugar alcohols such as sorbitol, mannitol, xylitol, maltitol, lactitol, hydrogenated isomaltulose and hydrogenated starch hydrolyzates.

The modified release rate noted above may be a fast release or a delayed release. The modified release of active agents such as caffeine may be obtained by encapsulation, partial encapsulation or partial coating, entrapment or absorption with high or low water soluble materials or water insoluble materials. The procedures for modifying the active agent include spray drying, spray chilling, fluid bed coating, coacervation, extrusion and other agglomerating and standard encapsulating techniques. The active agents also may be absorbed onto an inert or water-insoluble material. Active agents may be modified in a multiple step process comprising any of the processes, or a combination of the processes noted. Prior to encapsulation, active agents may also be combined with bulk sweeteners including sucrose, dextrose, fructose, maltodextrin or other bulk sweeteners, as well as sugar alcohols such as sorbitol, mannitol, xylitol, maltitol, lactitol, hydrogenated isomaltulose and hydrogenated starch hydrolyzates.

Prior to encapsulation, active agents such as caffeine may be combined with high-intensity sweeteners, including but not limited to thaumatin, aspartame, alitame, acesulfame K, saccharin acid and its salts, glycyrrhizin, cyclamate and its salts, stevioside and dihydrochalcones. Co-encapsulation of active agents along with a high-intensity sweetener may reduce the poor taste qualities of active agents and control the sweetener release with active agents. This can improve the quality of the gum product and increase consumer acceptability.

Preferably, the physically modified active agents such as caffeine are mixed with a panning syrup and then applied as a chewing gum coating. The coating is applied by panning techniques that may use sugars for a sugar panned product or may use sorbitol, xylitol, or other polyols to make either a soft or hard shell sugarless panned product. By adding physically modified active agents to a gum coating, the active agents will not be available in the mouth for tasting, but carried with the carbohydrate used in the coating and ingested into the digestive system, where the active agents can be absorbed systemically for its effect. This technique significantly reduces the overall poor quality taste of active agents as it is masked by the encapsulant in the mouth during chewing, and results in a gum product having increased consumer acceptability.

DETAILED DESCRIPTION OF THE PREFERRED EMBODIMENTS

Caffeine is a natural chemical found in a variety of food products such as coffee, tea, cocoa, chocolate, and various other beverages. Caffeine is known as an effective stimulant to increase energy and reduce drowsiness. Caffeine has a naturally bitter taste. The bitterness, however, actually improves the flavor perception of some beverages such as coffee and carbonated beverages.

When caffeine is added to stick chewing gum at a level of about 0.2% to about 5%, caffeine imparts an intense bitterness to the chewing gum that lasts throughout the chewing period. The higher the level used, the stronger the bitterness. At about 0.2%, which is about 5 mg per 2.7 gram stick, the bitterness is below the threshold limit and is not readily discernible. Taste limits in stick chewing gum are generally about 0.4% (10 mg) to about 4% (100 mg) of caffeine in a stick of gum. The 60–80 mg level of caffeine is about the level of caffeine found in a conventional cup of coffee. The target level of caffeine in stick gum is about 40 mg per stick, with a range of about 25–60 mg, so that a five stick package of gum would contain about 200 mg of caffeine, or the equivalent of caffeine in two strong cups of coffee. However, at this level caffeine bitterness overwhelms the flavor initially and lasts throughout the chewing period.

For coated pellet gum, piece weight is generally about 1.5 grams per piece. However, one coated piece of gum is about equal to ½ piece of stick gum. Two pellets are equivalent to a stick of gum, and together weigh about 3 grams. The above-noted target level of 40 mg per stick is equivalent to 20 mg per coated piece, or a range of about 12 to 30 mg caffeine per piece. This is about 0.8% to about 2% caffeine in a piece of coated gum, or a target level of 1.3%.

Caffeine is not a highly water soluble substance and, therefore, has a moderately slow release from stick chewing gum. Caffeine is 2.1% soluble in water at room temperature, 15% soluble in water at 80° C. and 40% soluble in boiling water. This gives caffeine a moderately slow release as shown below:

| Chewing Time | % Caffeine Release |
|---|---|
| 0 min | — |
| 5 min | 56 |
| 10 min | 73 |
| 20 min | 88 |
| 40 min | 97 |

Generally, highly water soluble ingredients in stick gum are about 80–90% released after only five minutes of chewing. For caffeine, only about 50% is released, while the other 50% remains in the gum after five minutes of chewing. After 20 minutes almost 90% of caffeine is released.

Even if caffeine is dissolved in hot water and mixed in the stick gum, when the gum is cooled or kept at room temperature, caffeine may return to its normal crystalline state and release at the same rate as shown above.

When unmodified caffeine is added to a coating of a coated gum piece, the coating, which is very water soluble and is very easily dissolved in the mouth, will dissipate in the mouth very quickly. This will give a fast release of caffeine into the mouth, giving a very strong bitter taste. This bitter taste from the caffeine will remain in the mouth even after the caffeine has been ingested. However, when an encapsulated caffeine is employed in the gum coating, upon dissipation of the encapsulated caffeine in the mouth the encapsulating agent masks or shields the caffeine from the taste receptors of the mouth, thus reducing the bitterness experienced by the chewer. After being ingested into the digestive tract, the caffeine will be released from its encapsulating agent and will be absorbed and effective as a stimulant. Accordingly, the employment of encapsulated caffeine in a chewing gum coating allows for the delivery of caffeine to a user in a manner which does not result in the user experiencing significant bitterness, and at a minimum results in the user experiencing significantly less bitterness than would be experienced utilizing unencapsulated caffeine in the coating. Furthermore, the use of encapsulated caffeine in a gum coating allows for significantly higher levels of caffeine to be provided in a given piece of coated gum without the chewer experiencing the bitterness associated with the caffeine than would otherwise be achievable in the absence of caffeine encapsulation. This would allow for delivery of caffeine levels on the order of that found in a cup of coffee to be provided in only two, or possibly even only one, piece of coated gum, without the chewer experiencing the bitterness which would otherwise result in the absence of encapsulating the caffeine. Additionally, the encapsulating agent may be selected to provide a time delay of release of the caffeine, or two or more encapsulating agents may be utilized having different release rates to provide a selectively controlled time release of the caffeine subsequent to ingestion of the caffeine.

Caffeine salt compounds such as caffeine citrate, caffeine sodium benzoate, caffeine sodium salicylate, which may be more water soluble and less bitter than caffeine, may also be encapsulated or entrapped for use in a chewing gum coating in accordance with the present invention.

Other active agents or medicaments that may have a bitter or unpleasant off-taste may be included in the present invention. By the terms "active agent" the present invention refers to a compound that has a desired therapeutic or physiological effect once ingested and/or metabolized. The therapeutic effect may be one which decreases the growth of a xenobiotic or other gut flora or fauna, alters the activity of an enzyme, provides the physical relief from a malady (e.g., diminishes pain, acid reflux or other discomfort), has an effect on the brain chemistry of molecules that determine mood and behavior. Of course these are just examples of what is intended by therapeutic effect. Those of skill in the art will readily recognize that a particular agent has or is associated with a given therapeutic effect.

The active agent may be any agent that is traditionally used as a medicament and lends itself to being administered through the oral cavity. Such active agents may be vitamins, chemotherapeutics; antimycotics; oral contraceptives, nicotine or nicotine replacement agents, minerals, analgesics, antacids, muscle relaxants, antihistamines, decongestants, anesthetics, antitussives, diuretics, anti-inflammatories, antibiotics, antivirals, psychotherapeutic agents, anti-diabetic agents and cardiovascular agents, nutraceuticals and nutritional supplements.

Vitamins and co-enzymes that may be delivered using this invention include but are not limited to water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs, vitamin A and the carotenoids, retinoic acid, vitamin E and vitamin K.

Examples of chemotherapeutics agents include but are not limited to cisplatin (CDDP), procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Antimicrobial agents that may be used include but are not limited to naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, β-lactamase inhibitors; meziocillin, piperacillin, aztreonam, norfloxacin, trimethoprim, ceftazidime, dapsone.

Antifungal agents that may be delivered include but are not limited to ketoconazole, fluconazole, nystatin, itraconazole, clomitrazole, and amphotericin B. Antiviral agents that may be used include but are not limited to acyclovir, trifluridine, idoxorudine, foscarnet, ganciclovir, zidovudine, dideoxycytosine, dideoxyinosine, stavudine, famciclovir, didanosine, zalcitabine, rifimantadine, and cytokines.

Antacids include cimetidine, ranitidine, nizatidine, famotidine, omeprazole, bismuth antacids, metronidazole antacids, tetracycline antacids, clarthromycin antacids, hydroxides of aluminum, magnesium, sodium bicarbonates, calcium bicarbonate and other carbonates, silicates, and phosphates.

Antihistamines are represented by but are not limited to cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prilamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine.

Decongestants and antitussives include agents such as dextromethorphan, levopropoxyphene napsylate, noscapine, carbetapentane, caramiphen, chlophedianol, pseudoephedrine hydrochloride, diphenhydramine, glaucine, pholcodine, and benzonatate.

Anesthetics include etomidate, ketamine, propofol, and benodiazapines (e.g., chlordiazepoxide, diazepam, clorezepate, halazepam, flurazepam, quazepam, estazolam, triazolam, alprozolm, midazolam, temazepam, oxazepam, lorazepam), benzocaine, dyclonine, bupivacaine, etidocaine, lidocaine, mepivacaine, promoxine, prilocaine, procaine, proparcaine, ropivacaine, tetracaine. Other useful agents may include amobartital, aprobarbital, butabarbital, butalbital mephobarbital, methohexital, pentobarbital, phenobarbital, secobarbital, thiopental, paral, chloral hydrate, ethchlorvynol, clutethimide, methprylon, ethinamate, and meprobamate.

Analgesics, include opioids such as morphine, mepidine, dentanyl, sufentranil, alfentanil, aspirin, acetaminophen, ibuprofen, indomethacine, naproxen, atrin, isocome, midrin, axotal, firinal, phrenilin, ergot and ergot derivatives (wigraine, cafergot, ergostat, ergomar, dihydroergotamine), imitrex.

Diuretics include but are not limited to acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, amiloride, triamterene, sprionolactone, canrenone, and potassium canrenoate.

Anti-inflammatories include but are not limited to salicylic acid derivatives (e.g. aspirin) paraminophenol derivative (e.g. acetaminophen) indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone).

Psychotherapeutic agents include thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, eldepryl.

Cardiovascular agents include but are not limited to nitroglycerin, isosorbide dinitrate, sodium nitroprisside, captopril, enalapril, enalaprilat, quinapril, lisinopril, ramipril, losartan, amrinone, lirinone, vesnerinone, hydralazine, nicorandil, prozasin, doxazosin, bunazosin, tamulosin, yohimbine, propanolol, metoprolol, nadolol, atenolol, timolol, esmolol, pindolol, acebutolol, labetalol, phentolamine, carvedilol, bucindolol, verapamil, nifedipine, amlodipine and dobutamine.

It is envisioned that depending on the active agent or medicament, the resultant chewing gum can be used to treat inter alia: coughs, colds, motion sickness; allergies; fevers; pain; inflammation; sore throats; cold sores; migraines; sinus problems; diarrhea; diabetes, gastritis; depression; anxiety, hypertension; angina and other maladies and symptoms. Also these gums may be useful in ameliorating cravings in substance abuse withdrawal. Specific active agents or medicaments include by way of example and limitation: caffeine, aspirin, acetaminophen; ibuprofen; cimetidine, ranitidine, famotidine, dramamine, omeprazole, dyclonine, chlorpheniramine maleate, pseudoephedrine hydrochloride, dextromethorphan, benzocaine, naproxen, and nicotine.

Compositions that may be formulated into a suitable chewing gum formulation are described in, for examples, U.S. Pat. No. 5,858,423; U.S. Pat. No. 5,858,413; U.S. Pat. No. 5,858,412 and U.S. Pat. No. 5,858,383. Additionally, Goodman and Gilman's "The Pharmaceutical Basis of Therapeutics" (Eds. Hardman et al., Publ. McGraw Hill, N.Y.) provides comprehensive guidance of useful drugs and their mechanisms of action. Medicated chewing gums have been particularly effective in the delivery of agents such as nicotine as described in for example, U.S. Pat. No. 5,866,179; and U.S. Pat. No. 5,889,028. U.S. Pat. No. 5,846,557 describes general chewing gum compositions containing cough suppressing agents. These patents are incorporated herein by reference as providing a teaching of the incorporation of medicinal agents into oral chewable formulations. It should be understood that the present chewing gum formulation(s) are not limited to the agents listed herein above, indeed any medicinal or other active agent that lends itself to ingestion may be formulated into the chewing gum formulations of the present invention.

Nutraceuticals and nutritional supplements may also be added to chewing gums as active agents. Among these are herbs and botanicals that include, but are not limited to capsicum, chamomile, cat's claw, echinacea, garlic, ginger, ginko, various ginseng, green tea, golden seal, kava kava, nettle, passion flower, saw palmetto, St. John's wort, and valerian. Also included are mineral supplements such as calcium, copper, iodine, iron, magnesium, manganese, molybdenum, phosphorous, and selenium. Other nutraceuticals that also can be added to chewing gum as active agents are fructo-oligosaccharides, glucosamine, grapeseed extract, guarana, inulin, phytosterols, phytochemicals, isoflavones, lecithin, lycopene, oligofructose, polyphenol and psyllium as well as weight loss agents such as chromium picolinate and phenylpropanolamine.

Preferably, the active agents or medicaments are contained in the chewing gum formulation at levels of approximately 50 micrograms to 500 milligrams. The specific levels will depend on the active ingredient. For example, if chromium picolinate is the active ingredient in an embodiment, it would be present at a level of 50 micrograms per serving (3.0 grams/two pieces of gum); aspirin would be preset at a level up to 325 milligrams per 3.0 gram serving (two pieces). To obtain the higher levels, additional coatings in the gum will be needed. This will increase piece size for a two piece serving size.

If the agent is a stimulant, such as caffeine, to be used to enhance performance then the chewing gum would be chewed, in a preferred embodiment ten minutes or less before the performance. It has been surprisingly found that with an extra five minutes of chewing a caffeine-containing chewing gum a high level of alertness is achieved.

The medicament or active agent can be contained in a variety of different chewing gum compositions. Referring now to the chewing gum, pursuant to the present invention, the chewing gum including the medicament or active agent may be based on a variety of different chewing gums that are known. For example, the chewing gums can be low or high moisture, sugar or sugarless, wax containing or wax free, low calorie (via high base or low calorie bulking agents), and/or may contain dental agents.

Pursuant to the present invention, depending on the active agent or medicament, the dosing regiment will change. For example, it the medicament is an analgesic, the chewing gum would be taken on an as needed basis. Of course, similar to the oral administration of an analgesic, there would be restrictions on the number of pieces of chewing gum chewed, for example, not more often than two pieces every four hours and not more often than four to five times a day.

Physical modifications of the active agent such as caffeine by encapsulation with a highly water soluble substrate will increase its release in stick chewing gum as well as from the gum coating by increasing the solubility or dissolution rate of caffeine. However, preferably the active agent such as caffeine may also be encapsulated or entrapped to give a delayed release from stick chewing gum and from a gum coating. Any standard technique which gives partial or full encapsulation of the active agent can be used. These techniques include, but are not limited to, spray drying, spray chilling, fluid-bed coating and coacervation. These encapsulation techniques may be used individually in a single step process or in any combination in a multiple step process.

Active agents such as caffeine may be encapsulated with sweeteners, more specifically high-intensity sweeteners such as thaumatin, dihydrochalcones, acesulfame K, aspartame, sucralose, alitame, saccharin and cyclamates. These can also have the effect of reducing unpleasant tastes such as bitterness. Additional bitterness inhibitors or taste maskers can also be combined with active agents and sweeteners to give a reduced unpleasant taste such as bitterness with delayed release active agent(s).

The encapsulation techniques described herein are standard coating techniques and generally give varying degrees of coating from partial to full coating, depending on the coating composition used in the process.

Generally, compositions that have high organic solubility, good film-forming properties and low water solubility give better delayed release of active agents such as caffeine, while compositions that have high water solubility give better fast release. Such low water-solubility compositions include acrylic polymers and copolymers, carboxyvinyl polymer, polyamides, polystyrene, polyvinyl acetate, polyvinyl acetate phthalate, polyvinylpyrrolidone and waxes. Although all of these materials are possible for encapsulation of active agents such as caffeine, only food-grade materials should be considered. Two standard food-grade coating materials that are good film formers but not water soluble are shellac and Zein. Others which are more water soluble, but good film formers, are materials like agar, alginates, a wide range of cellulose derivatives like ethyl cellulose, methyl cellulose, sodium hydroxymethyl cellulose, and hydroxypropylmethyl cellulose, dextrin, gelatin, and modified starches. These ingredients, which are generally approved for food use, may give a fast release when used as an encapsulant. Other encapsulants like acacia or maltodextrin can also encapsulate active agent(s) and give a fast release rate in gum.

The amount of coating or encapsulating material on the active agent also may control the length of time for its release from chewing gum. Generally, the higher the level of coating and the lower the amount of active agent, the slower the release during mastication with low water soluble compositions. The release rate is generally not instantaneous, but gradual over an extended period of time for stick gum. When used in a coating, delayed release allows the active agent to be masked in the mouth before being ingested, thus reducing bitterness or other unpleasant tastes. To obtain the delayed release, the encapsulant should be a minimum of about 20% of the coated active. Preferably, the encapsulant should be a minimum of about 30% of the coated active, and most preferably should be a minimum of about 40% of the coated active.

Another method of giving a modified release of active agents such as caffeine and the other agents described herein is agglomeration with an agglomerating agent which partially coats the active agents. This method includes the step of mixing active agents and an agglomerating agent with a small amount of water or solvent. The mixture is prepared in such a way as to have individual wet particles in contact with each other so that a partial coating can be applied. After the water or other solvent is removed, the mixture is ground and used as a powdered active agent.

Materials that can be used as the agglomerating agent are the same as those used in encapsulation mentioned previously. Some of the better agglomerating agents for delayed release are the organic polymers like acrylic polymers and copolymers, polyvinyl acetate, polyvinylpyrrolidone, waxes, shellac and Zein. Other agglomerating agents are not as effective in giving a delayed release as are the polymers, waxes, shellac and Zein, but can be used to give some delayed release. Other agglomerating agents include, but are not limited to, agar, alginates, a wide range of water soluble cellulose derivatives like ethyl cellulose, methyl cellulose, sodium hydroxymethyl cellulose, hydroxypropylmethyl cellulose, dextrin, gelatin, modified starches, and vegetable gums like guar gum, locust bean gum and carrageenan. Even though the agglomerated active agent such as caffeine is only partially coated, when the quantity of coating is increased compared to the quantity of the active agent, the release can also be modified. The level of coating used in the agglomerated product is a minimum of about 5%. Preferably, the coating level is a minimum of about 15% and more preferably about 20%. Depending on the agglomerating agent, a higher or lower amount of agent may be needed to give the desired release of the active agent.

Caffeine or other active agents may be coated in a two-step process or a multiple step process. Caffeine or other active agents may be encapsulated with any of the materials as described previously and then the encapsulated caffeine or other active agents can be agglomerated as previously described to obtain an encapsulated/agglomerated/caffeine or other active agent product that could be used in chewing gum to give a delayed release of the caffeine or other active agent.

In another embodiment of this invention, caffeine or other active agent may be absorbed onto another component which is porous and become entrapped in the matrix of the porous component. Common materials used for absorbing caffeine or other active agent include, but are not limited to, silicas, silicates, pharmasorb clay, sponge-like beads or microbeads, amorphous carbonates and hydroxides, including aluminum and calcium lakes, all of which result in a delayed release of caffeine or other active agent.

Depending on the type of absorbent materials and how it is prepared, the amount of caffeine or other active agent that can be loaded onto the absorbent will vary. Generally materials like polymers or sponge-like beads or microbeads, amorphous sugars and alditols and amorphous carbonates and hydroxides absorb about 10% to about 40% of the weight of the absorbent. Other materials like silicas and pharmasorb clays may be able to absorb about 20% to about 80% of the weight of the absorbent.

The general procedure for absorbing caffeine or other active agent onto the absorbent is as follows. An absorbent like fumed silica powder can be mixed in a powder blender and a solution of caffeine or other active agent can be sprayed onto the powder as mixing continues. The aqueous solution can be about 1 to 2% solids, and higher solid levels to 15–30% may be used if temperatures up to 90° C. are used. Generally water is the solvent, but other solvents like alcohol could also be used if approved. As the powder mixes, the liquid is sprayed onto the powder. Spraying is stopped before the mix becomes damp. The still free-flowing powder is removed from the mixer and dried to remove the water or other solvent, and is then ground to a specific particle size.

After the caffeine or other active agent is absorbed or fixed onto an absorbent, the fixative/active agent can be coated by encapsulation. Either full or partial encapsulation may be used, depending on the coating composition used in the process. Full encapsulation may be obtained by coating with a polymer as in spray drying, spray chilling, fluid-bed coating, coacervation, or any other standard technique. A partial encapsulation or coating can be obtained by agglomeration of the fixative/active agent mixture using any of the materials discussed above.

Another form of encapsulation is by entrapment of an ingredient by fiber extrusion or fiber spinning into a polymer. Polymers that can be used for extrusion are PVAC, hydroxypropyl cellulose, polyethylene and other types of plastic polymers. A process of encapsulation by fiber extrusion is disclosed in U.S. Pat. No. 4,978,537, which is hereby incorporated by reference. The water insoluble polymer may be preblended with caffeine or other active agents prior to fiber extrusion, or may be added after the polymer is melted. As the extrudate is extruded, it results in small fibers that are cooled and ground. This type of encapsulation/entrapment generally gives a very long, delayed release of an active ingredient.

The four primary methods to obtain a treated caffeine or other active agent are: (1) encapsulation by spray drying, fluid-bed coating, spray chilling and coacervation to give full or partial encapsulation, (2) agglomeration to give partial encapsulation, (3) fixation or absorption which also gives partial encapsulation, and (4) entrapment into an extruded compound. These four methods, combined in any usable manner which physically modifies caffeine or other active agents dissolvability or modifies the release of caffeine or other active agents, are included in this invention.

After the active agent is treated it is used in the coating/panning of a pellet chewing gum. Pellet or ball gum is prepared as conventional chewing gum, but formed into pellets that are pillow shaped or into balls. The pellets/balls can then be sugar coated or panned by conventional panning techniques to make a unique sugar coated pellet gum.

Treated active agent(s) can be easily dispersed in a sugar solution prepared for sugar panning. Preferably, treated active agent(s) can be added as a powder blended with other powders often used in some types of conventional panning procedures often called dry charging. The weight of the coating may be about 20% to about 50% of the weight of the finished gum product, but higher levels of coating may be used when high doses of active agents are needed.

Conventional panning procedures generally coat with sucrose, but recent advances in panning have allowed the use of other carbohydrate materials to be used in the place of sucrose. Some of these components include, but are not limited to, dextrose, maltose, palatinose, xylitol, lactitol, maltitol, hydrogenated isomaltulose and other new alditols or a combination thereof. These materials may be blended with panning modifiers including, but not limited to, gum arabic, gum talha, maltodextrins, corn syrup, gelatin, cellulose type materials like carboxymethyl cellulose or hydroxymethyl cellulose, starch and modified starches, vegetable gums like alginates, locust bean gum, guar gum, and gum tragacanth, insoluble carbonates like calcium carbonate or magnesium carbonate and talc. Antitack agents may also be added as panning modifiers which allow for the use of a variety of carbohydrates and sugar alcohols in the development of new panned or coated gum products. Flavors, sweeteners and cooling agents may also be added with the coating and with treated active agents to yield unique product characteristics.

The previously described encapsulated, agglomerated or absorbed active agent may readily be coated onto a chewing gum composition. The remainder of the chewing gum ingredients are non-critical to the present invention. That is, the treated particles of active agent can be coated onto conventional chewing gum formulations in a conventional manner. Treated active agent may be coated onto a sugar chewing gum or a sugarless chewing gum.

In general, a chewing gum composition typically comprises a water-soluble bulk portion, a water-insoluble chewable gum base portion and typically water-insoluble flavoring agents. The water-soluble portion dissipates with a portion of the flavoring agent over a period of time during chewing. The gum base portion is retained in the mouth throughout the chew.

The insoluble gum base generally comprises elastomers, resins, fats and oils, waxes, softeners and inorganic fillers. Elastomers may include polyisobutylene, isobutylene-isoprene copolymer and styrene butadiene rubber, as well as natural latexes such as chicle. Resins include polyvinylacetate and terpene resins. Fats and oils may also be included in the gum base, including tallow, hydrogenated and partially hydrogenated vegetable oils, and cocoa butter. Commonly employed waxes include paraffin, microcrystalline and natural waxes such as beeswax and carnauba. According to the preferred embodiment of the present invention, the insoluble gum base constitutes between about 5% and about 95% by weight of the gum. More preferably the insoluble gum base comprises between about 10% and about 50% by weight of the gum, and most preferably between about 20% and about 45% by weight of the gum. When high levels of gum coatings are needed, gum may comprise up to 95% of the gum center formula.

The gum base typically also includes a filler component. The filler component may be calcium carbonate, magnesium carbonate, talc, dicalcium phosphate or the like. The filler may constitute between about 5% and about 60% by weight of the gum base. Preferably, the filler comprises about 5% to about 50% by weight of the gum base.

Gum bases typically also contain softeners, including glycerol monostearate and glycerol triacetate. Further, gum bases may also contain optional ingredients such as antioxidants, colors, and emulsifiers. The present invention contemplates employing any commercially acceptable gum base.

The water-soluble portion of the chewing gum may further comprise softeners, sweeteners, flavoring agents and combinations thereof. Softeners are added to the chewing gum in order to optimize the chewability and mouth feel of the gum. Softeners, also known in the art as plasticizers or plasticizing agents, generally constitute between about 0.5% and about 15% by weight of the chewing gum. Softeners contemplated by the present invention include glycerin, lecithin and combinations thereof. Further, aqueous sweetener solutions such as those containing sorbitol, hydrogenated starch hydrolyzates, corn syrup and combinations thereof may be used as softeners and binding agents in gum.

As mentioned above, the treated active agent of the present invention may be used in sugar or sugarless gum formulations. Sugar sweeteners generally include saccharide-containing components commonly known in the chewing gum art which comprise, but are not limited to, sucrose, dextrose, maltose, dextrin, dried invert sugar, fructose, levulose, galactose, corn syrup solids and the like, alone or in any combination. Sugarless sweeteners include components with sweetening characteristics but which are devoid of the commonly known sugars and comprise, but are not limited to, sugar alcohols such as sorbitol, mannitol, xylitol, hydrogenated starch hydrolyzates, maltitol and the like, alone or in any combination.

Depending on the particular active agent release profile, the treated active agent of the present invention can also be used in combination with uncoated high-potency sweeteners or with high-potency sweeteners coated with other materials and by other techniques. Also, untreated active agents could be added to the coating.

A flavoring agent may also be present in the chewing gum in an amount within the range of from about 0.1% to about 10%, preferably from about 0.5% to about 5%, by weight of the gum. The flavoring agents may comprise essential oils, synthetic flavors, or mixtures thereof including, but not limited to oils derived from plants and fruits such as citrus oils, fruit essences, peppermint oil, spearmint oil, clove oil, oil of wintergreen, anise, and the like. Artificial flavoring components are also contemplated for use in gums of the present invention. Those skilled in the art will recognize that natural and artificial flavoring agents may be combined in any sensorally acceptable blend. All such flavors and flavor blends are contemplated by the present invention.

Optional ingredients such as colors, emulsifiers and other pharmaceutical agents may be added to the chewing gum.

In general, chewing gum is manufactured by sequentially adding the various chewing gum ingredients to a commercially available mixer known in the art. After the ingredients have been thoroughly mixed, the gum mass is discharged from the mixer and shaped into the desired form such as extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

As noted above, the coating may contain ingredients such as flavoring agents, as well as artificial sweeteners and dispersing agents, coloring agents, film formers and binding agents. Flavoring agents contemplated by the present invention include those commonly known in the art such as essential oils, synthetic flavors or mixtures thereof, including but not limited to oils derived from plants and fruits such as citrus oils, fruit essences, peppermint oil, spearmint oil, other mint oils, clove oil, oil of wintergreen, anise and the like. The flavoring agents may be used in an amount such that the coating will contain from about 0.2% to about 3% flavoring agent, and preferably from about 0.7% to about 2.0% flavoring agent.

Artificial sweeteners contemplated for use in the coating include but are not limited to synthetic substances, saccharin, thaumatin, alitame, saccharin salts, aspartame, sucralose and acesulfame-K. The artificial sweetener may be added to the coating syrup in an amount such that the coating will contain from about 0.05% to about 0.5%, and preferably from about 0.10% to about 0.3% artificial sweetener.

Dispersing agents are often added to syrup coatings for the purpose of whitening and tack reduction. Dispersing agents contemplated by the present invention to be employed in the coating syrup include titanium dioxide, talc, or any other antistick compound. Titanium dioxide is a presently preferred dispersing agent of the present invention. The dispersing agent may be added to the coating syrup in amounts such that the coating will contain from about 0.1% to about 1.0%, and preferably from about 0.3% to about 0.6% of the agent.

Coloring agents are preferably added directly to the syrup in the dye or lake form. Coloring agents contemplated by the present invention include food quality dyes. Film formers preferably added to the syrup include methyl cellulose, gelatins, hydroxypropyl cellulose, ethyl cellulose, hydroxyethyl cellulose, carboxymethyl cellulose and the like and combinations thereof. Binding agents may be added either as an initial coating on the chewing gum center or may be added directly into the syrup. Binding agents contemplated by the present invention include gum arabic, gum talha (another type of acacia), alginate, cellulosics, vegetable gums and the like.

The coating is initially present as a liquid syrup which contains from about 30% to about 80% or 85% of the coating ingredients previously described herein, and from about 15% or 20% to about 70% of a solvent such as water. In general, the coating process is carried out in a rotating pan. Sugar or sugarless gum center tablets to be coated are placed into the rotating pan to form a moving mass.

The material or syrup which will eventually form the coating is applied or distributed over the gum center tablets. Flavoring agents may be added before, during and after applying the syrup to the gum centers. Once the coating has dried to form a hard surface, additional syrup additions can be made to produce a plurality of coatings or multiple layers of hard coating.

In a hard coating panning procedure, syrup is added to the gum center tablets at a temperature range of from about 100° F. to about 240° F. Preferably, the syrup temperature is from about 130° F. to about 200° F. throughout the process in order to prevent the polyol or sugar in the syrup from crystallizing. The syrup may be mixed with, sprayed upon, poured over, or added to the gum center tablets in any way known to those skilled in the art.

In general, a plurality of layers is obtained by applying single coats, allowing the layers to dry, and then repeating the process. The amount of solids added by each coating step depends chiefly on the concentration of the coating syrup. Any number of coats may be applied to the gum center tablet. Preferably, no more than about 75 coats are applied to the gum center tablets. More preferably, less than about 60 coats are applied and most preferably, about 30 to about 60 coats are applied. In any event, the present invention contemplates applying an amount of syrup sufficient to yield a coated comestible containing about 10% to about 65% coating. Preferably, the final product will contain from about 20% to about 50% coating. Where higher dosage of an active agent is needed, the final product may be higher than 50% coating.

Those skilled in the art will recognize that in order to obtain a plurality of coated layers, a plurality of premeasured aliquots of coating syrup may be applied to the gum center tablets. It is contemplated, however, that the volume of aliquots of syrup applied to the gum center tablets may vary throughout the coating procedure.

Once a coating of syrup is applied to the gum center tablets, the present invention contemplates drying the wet syrup in an inert medium. A preferred drying medium comprises air. Preferably, forced drying air contacts the wet syrup coating in a temperature range of from about 70° to about 115° F. More preferably, the drying air is in the temperature range of from about 80° to about 100° F. The invention also contemplates that the drying air possess a relative humidity of less than about 15 percent. Preferably, the relative humidity of the drying air is less than about 8 percent.

The drying air may be passed over and admixed with the syrup coated gum centers in any way commonly known in the art. Preferably, the drying air is blown over and around or through the bed of the syrup coated gum centers at a flow rate, for large scale operations, of about 2800 cubic feet per minute. If lower quantities of material are being processed, or if smaller equipment is used, lower flow rates would be used.

For many years, flavors have been added to a sugar coating of pellet gum to enhance the overall flavor of gum. These flavors include spearmint flavor, peppermint flavor, wintergreen flavor, and fruit flavors. These flavors are generally preblended with the coating syrup just prior to applying it to the core or added together to the core in one or more coating applications in a revolving pan containing the cores. Generally, the coating syrup is very hot, about 150° to 200° F., and the flavor may volatilize if preblended with the coating syrup too early.

The concentrated coating syrup is applied to the gum cores as a hot liquid, the sugar or polyol allowed to crystallize, and the coating then dried with warm, dry air. This is repeated in about 30 to 80 applications to obtain a hard shell coated product having an increased weight gain of about 50%. A flavor is applied with one, two, three or even four or more of these coating applications. Each time flavor is added, several non-flavored coatings are applied to cover the flavor before the next flavor coat is applied. This reduces volatilization of the flavor during the coating process.

For mint flavors such spearmint, peppermint and wintergreen, some of the flavor components are volatilized, but sufficient flavor remains to give a product having a strong, high impact flavor. Fruit flavors, that may contain esters, are more easily volatilized and may be flammable and/or explosive and therefore, generally these type of fruit flavors are not used in coatings.

In a preferred embodiment of this invention, a treated active agent such as caffeine is preblended with a gum arabic solution to become a paste and then applied to the cores. To reduce stickiness, the preblend may be mixed with a small amount of coating syrup before being applied. Forced air drying is then continued as the gum arabic binds the treated active agent to the cores. Then additional coatings are applied to cover the treated active agent and imbed the treated active agent in the coatings.

Gum Formulation Examples

The following examples of the invention and comparative examples are provided by way of explanation and illustration.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas for pellet centers are generally adjusted to a higher level of gum base to give a more consumer acceptable size of gum bolus.

Keeping this in mind, if a coating of about 25% of the total product is added to a pellet core as sugar or polyols, the gum base in the pellet core should also be increased by 25%. Likewise, if a 33% coating is applied, the base levels should also be increased by 33%. As a result, gum centers are usually formulated with about 25% to about 40% gum base with a corresponding decrease in the other ingredients except flavor. Generally flavors increase with the level of gum base as the base tends to bind flavors into the gum and more flavor is needed to give a good flavorful product. However flavors can also be added to the coating to give increased flavor impact and more flavor perception.

Some typical sugar type gum center formulations are shown in Table 1.

TABLE 1

| | \(WEIGHT PERCENT\) | | | | | |
|---|---|---|---|---|---|---|
| | EX. 1 | EX. 2 | EX. 3 | EX. 4 | EX. 5 | EX. 6 |
| SUGAR | 52.0 | 49.0 | 48.0 | 44.0 | 41.0 | 39.0 |
| GUM BASE | 26.0 | 30.0 | 35.0 | 26.0 | 30.0 | 35.0 |
| CORN SYRUP | 20.0 | 19.0 | 15.0 | 18.0 | 17.0 | 14.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONOHYDRATE | — | — | — | 10.0 | 10.0 | 10.0 |

Encapsulated caffeine can then be used in the coating formula on the various pellet gum formulations. The following Table 2 shows some sugar and dextrose type formulas:

TABLE 2

| | (DRY WEIGHT PERCENT) | | | | | | | | | |
|---|---|---|---|---|---|---|---|---|---|---|
| | EX. 7 | EX. 8 | EX. 9 | EX. 10 | EX. 11 | EX. 12 | EX. 13 | EX. 14 | EX. 15 | EX. 16 |
| SUGAR | 95.1 | 94.4 | 93.1 | 94.9 | 94.1 | 92.6 | | | | |
| DEXTROSE MONOHYDRATE | | | | | | | 96.6 | 94.4 | 96.2 | 93.5 |
| GUM TALHA | 2.0 | 3.0 | 4.0 | 2.0 | 3.0 | 4.0 | 1.5 | 3.0 | 1.5 | 3.0 |
| TITANIUM DIOXIDE | 0.5 | 1.0 | 1.0 | — | — | — | 0.5 | 1.0 | — | — |
| CALCIUM CARBONATE | — | — | — | 0.5 | 1.0 | 2.0 | — | — | 1.0 | 2.0 |
| FLAVOR | 0.3 | 0.5 | 0.8 | 0.5 | 0.8 | 0.3 | 0.3 | 0.5 | 0.2 | 0.4 |
| WAX | 0.1 | 0.1 | 0.1 | 0.1 | 0.1 | 0.1 | 0.1 | 0.1 | 0.1 | 0.1 |
| ACTIVE ENCAPSULATED CAFFEINE | 2.0 | 1.0 | 1.0 | 2.0 | 1.0 | 1.0 | 1.0 | 1.0 | 1.0 | 1.0 |

The above formulations are made by making a syrup by dissolving the sugar and gum talha in solution at about 75% solids at boiling, and suspending titanium dioxide or calcium carbonate in this syrup. Encapsulated caffeine and flavor are not mixed with the hot syrup, but added at low levels with one or more coats. After the final coats are applied and dried, wax is applied to give a smooth polish. This process gives a hard shell coating.-

A dry charge blend of powdered sugar, dextrose monohydrate or gum talha may be used. When encapsulated caffeine is added to the coating, it may be preblended with the dry charge material. The dry charge powder material is applied to the surface after the liquid syrup to help dry the surface before applying another coating. A dry charge may be used to build up a coating, but then finished with a straight syrup to obtain a hard shell. Table 3 gives these types of formulas.

TABLE 3

(DRY WEIGHT PERCENT)

| | EX. 17 | EX. 18 | EX. 19 | EX. 20 | EX. 21 | EX. 22 |
|---|---|---|---|---|---|---|
| SUGAR | 75.5 | 80.4 | — | — | 85.5 | — |
| DEXTROSE MONOHYDRATE | — | — | 76.5 | 85.3 | — | 85.1 |
| POWDERED SUGAR | 20.0* | 15.0* | — | — | — | — |
| POWDER DEXTROSE | — | — | 20.0* | 10.0* | — | — |
| GUM TALHA POWDER | 2.0 | 3.0 | 2.0 | 3.0 | 8.0* | 8.0* |
| GUM TALHA SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| ACTIVE ENCAPSULATED CAFFEINE | 2.0 | 1.0 | 1.0 | 1.0 | 2.0 | 2.0 |

*Powder and/or crystalline sugar or gum talha blended with encapsulated caffeine may be used.

In Examples 17–20, gum talha is blended in the sugar syrup. In Examples 21 and 22, gum talha powder is dry charged after a gum talha solution is applied in the first stages of coating, then this is followed by a hard shell coating of sugar solution or dextrose solution.

Encapsulated caffeine may also be preblended with gum talha solution to form a paste, and to assist in drying when mixed with coating syrup. Preferably this should be done when the encapsulant is water insoluble. The gum talha/encapsulated caffeine should also be applied to the coating immediately after being preblended.

Gum talha may also be used in coating of sugarless gum centers. Like sugar gum centers, the base formulation can be increased in proportion to the amount of coating applied to the center. Formulations for low and high moisture gum can be used to make gum centers. Generally, the base level may be increased to 30–46% with the other ingredients proportionally reduced. Some typical gum formulas are in Table 4.

TABLE 4

(WEIGHT PERCENT)

| | EX. 23 | EX. 24 | EX. 25 | EX. 26 | EX. 27 | EX. 28 | EX. 29 |
|---|---|---|---|---|---|---|---|
| GUM BASE | 35.0 | 35.0 | 30.0 | 30.0 | 30.0 | 40.0 | 30.0 |
| CALCIUM CARBONATE | — | — | 5.0 | 10.0 | 15.0 | — | — |
| SORBITOL | 43.3 | 45.3 | 46.3 | 40.3 | 44.8 | 41.7 | 46.5 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0a) | 10.0a) |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 | a)Lycasin brand hydrogenated starch hydrolyzate used instead of sorbitol liquid

In the above center formulations, the high intensity sweetener used is aspartame. However other high intensity such as alitame, acesulfame K, salts of acesulfame, cyclamate and its salts, saccharin and its salts, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Gum talha is especially useful in sugarless coatings with xylitol, sorbitol, maltitol, lactitol, hydrogenated isomaltulose and erythritol. Gum talha acts as a binder, film former and hardener of the coated pellet. The following table gives formulas for a xylitol coating with encapsulated caffeine:

TABLE 5

(DRY WEIGHT PERCENT)

| | EX. 30 | EX. 31 | EX. 32 | EX. 33 | EX. 34 | EX. 35 |
|---|---|---|---|---|---|---|
| XYLITOL | 93.8 | 91.4 | 89.7 | 89.1 | 88.9 | 87.8 |
| GUM TALHA | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| ACTIVE ENCAPSULATED CAFFEINE | 1.0 | 1.0 | 1.0 | 1.0 | 1.0 | 1.0 |

*Lake color dispersed in xylitol solution
**Calcium carbonate used in place of titanium dioxide The above formulas are used to coat pellets by applying a xylitol/gum talha solution in multiple coats and air drying. Color or whitener is also mixed in the solution. After pellets have been coated and dried, talc and wax are added to give a polish.

As in sugar coating, some of the gum talha powder may be blended with powder xylitol for dry charging. Encapsulated caffeine may be added with the dry charge material. Also, a gum talha syrup may be made and used as a separate coating with encapsulated caffeine and dry charged.

Like xylitol, erythritol coating also requires a binder, film former, and hardener in the coating to make an acceptable product. The following formulations can be made:

TABLE 6

(DRY WEIGHT PERCENT)

|  | EX. 36 | EX. 37 | EX. 38 | EX. 39 | EX. 40 | EX. 41 |
|---|---|---|---|---|---|---|
| ERYTHRITOL | 92.8 | 90.5 | 88.2 | 89.1 | 87.4 | 85.8 |
| GUM TALHA | 5.0 | 7.0 | 8.5 | 8.5 | 10.0 | 12.0 |
| FLAVOR | 0.5 | 0.4 | 0.7 | 0.7 | 0.9 | 0.5 |
| TITANIUM DIOXIDE | 0.5 | 0.9 | — | 0.5 | 0.5 | 0.5 |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR | — | — | 1.4* | — | — | — |
| ACTIVE ENCAPSULATED CAFFEINE | 1.0 | 1.0 | 1.0 | 1.0 | 1.0 | 1.0 |

*Lake color dispersed in erythritol solution

The above formulas are used to coat pellets by applying a erythritol/gum talha solution in multiple coats and air drying. Color or whitener is also mixed in the solution. After pellets have been coated and dried, talc and wax are added to give a polish.

As in xylitol coating, some of the gum talha powder may be blended with powder erythritol for dry charging. Encapsulated caffeine may be added with the dry charge material. Also, a gum talha syrup may be made and used as a separate coating with encapsulated caffeine and dry charged.

For coating formulas based on sorbitol, maltitol, lactitol, and hydrogenated isomaltulose, gum talha can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. As above, encapsulated caffeine can be added with the dry charge. The following formulations may be used.

TABLE 7

(DRY WEIGHT PERCENT)

|  | EX. 42 | EX. 43 | EX. 44 | EX. 45 | EX. 46 | EX. 47 |
|---|---|---|---|---|---|---|
| SORBITOL | 93.8 | 90.9 | 86.1 | 85.8 | 75.1 | 68.5 |
| SORBITOL POWDER | 2.0 | 3.0 | 5.0 | 10.0 | 20.0 | 25.0 |
| GUM TALHA | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| ACTIVE ENCAPSULATED CAFFEINE | 1.0 | 1.0 | 1.0 | 1.0 | 1.0 | 1.0 |

Sorbitol powder is used to dry charge in the early stages of coating. Sorbitol, gum talha, and whitener is blended into a syrup and applied to pellets. After all coating is applied and dried, talc and wax are added to give a polish.

In a similar manner, coatings with maltitol, lactitol, and hydrogenated isomaltulose may be made in the coating formulas in Table 7 by replacing sorbitol with any one of the other polyols and sorbitol powder with the polyol powder. Like sorbitol, the other polyols may become sticky during the coating and drying process, so the dry powder charge with encapsulated caffeine may be needed to give the proper drying. In the later stages of the coating process less gum talha could be used and a more pure polyol syrup could be used to give a smooth surface. Also, the dry charge would only be used in the early stages of the coating process. A gum talha syrup may be made and used as a separate coating with encapsulated caffeine and dry charged.

In addition to dry charging with the specific polyol, other ingredients may be added to the dry charge to help absorb moisture. These materials could be inert such as talc, calcium carbonate, magnesium carbonate, starches, gums like gum talha or other moisture absorbing materials. Also, powdered sweeteners or flavors could be added with the dry charge.

Some polyols such as sorbitol, maltitol, lactitol, or hydrogenated isomaltulose are not sufficiently sweet compared to sugar or xylitol, so high intensity sweeteners may be added to the coating such as aspartame, acesulfame K, salts of acesulfame, cyclamate and its salts, saccharin and its salts, alitame, sucralose, thaumatin, monellin, dihydrochalcone, glycyrrhizin, and combinations thereof. If a hot syrup is applied, heat may degrade the sweetener so only stable sweeteners should be used. Generally high intensity sweeteners are added with the polyol/gum talha solution to obtain an even distribution in the coatings.

Liquid flavors generally are not added throughout the coating but at specific points throughout the process. When flavor is added, less air is used for drying until the flavor coating is covered by the next coatings and dried. Flavors may be various spearmint, peppermint, wintergreen, cinnamon, and fruit flavors to yield a wide variety of flavored chewing gum products.

For examples 48 and 49, the following sugar gum center formulation was made into pellet gum centers as 1 gram pieces:

|  | % |
|---|---|
| Base | 29.14 |
| Sugar | 47.10 |
| Calcium Carbonate | 11.48 |
| 39DE, 43Be Corn Syrup | 8.83 |
| Glycerin | 1.32 |
| Peppermint flavor | 1.32 |
| Encapsulated high intensity sweeteners | 0.81 |
|  | 100.0 |

COMPARATIVE EXAMPLE 48

The following formulas were used to prepare coating syrups for this example:

|  | Syrup 1 | Syrup 2 |
|---|---|---|
| Sugar | 4885 grams | 3500 grams |
| Water | 2177 grams | 1500 grams |
| Modified Starch | 206 grams | — |
| Titanium Dioxide | 101 grams | — |
| Caffeine | 131 grams | — |
| Total | 7500 grams | 5000 grams |

Free caffeine was dissolved in coating Syrup 1 and applied to about 12,000 grams of gum centers until a coating of about 0.3 grams per piece had been formed. Because of the limited solubility of caffeine in the coating syrup, and the need for higher levels of caffeine in the final product, four applications of an additional 18 grams of caffeine each, mixed with 100grams of Syrup 1 to form a slurry, were poured into the coating pan. Thus 203 grams of caffeine was applied. Thereafter the coating was finished with Syrup 2 to achieve a 1.5 gram piece weight, with a total yield of 18,000 grams of coated product. The theoretical percentage of caffeine in the final product was about 1.13%.

EXAMPLE 49

The following formulas were used to prepare coating syrups for this example:

|  | Syrup 3 | Syrup 4 |
| --- | --- | --- |
| Sugar | 5015 grams | 3500 grams |
| Water | 2178 grams | 1500 grams |
| Modified Starch | 206 grams | — |
| Titanium Dioxide | 101 grams | — |
| Total | 7500 grams | 5000 grams |
| Encapsulated Caffeine | 240 grams |  |

The encapsulated caffeine used in Syrup 3 was made by fluid bed coating caffeine with an alcoholic/Zein mixture to give an 80% active caffeine/20% Zein. This material was blended with a 40% solution of gum arabic and some of Syrup 3 at a ratio of 60 parts encapsulated caffeine to 100 parts gum arabic solution to 100 parts Syrup 3 to form a slurry, and applied in four stages with coating Syrup 3 to achieve a piece weight of about 1.3 grams. The total active caffeine applied was about 192 grams The gum was finished with Syrup 4 to achieve a piece weight of about 1.5 gram. The theoretical percentage of caffeine in the final product was about 1.07%. An analysis of the product showed an actual caffeine level of 1.13%.

Figure 1:
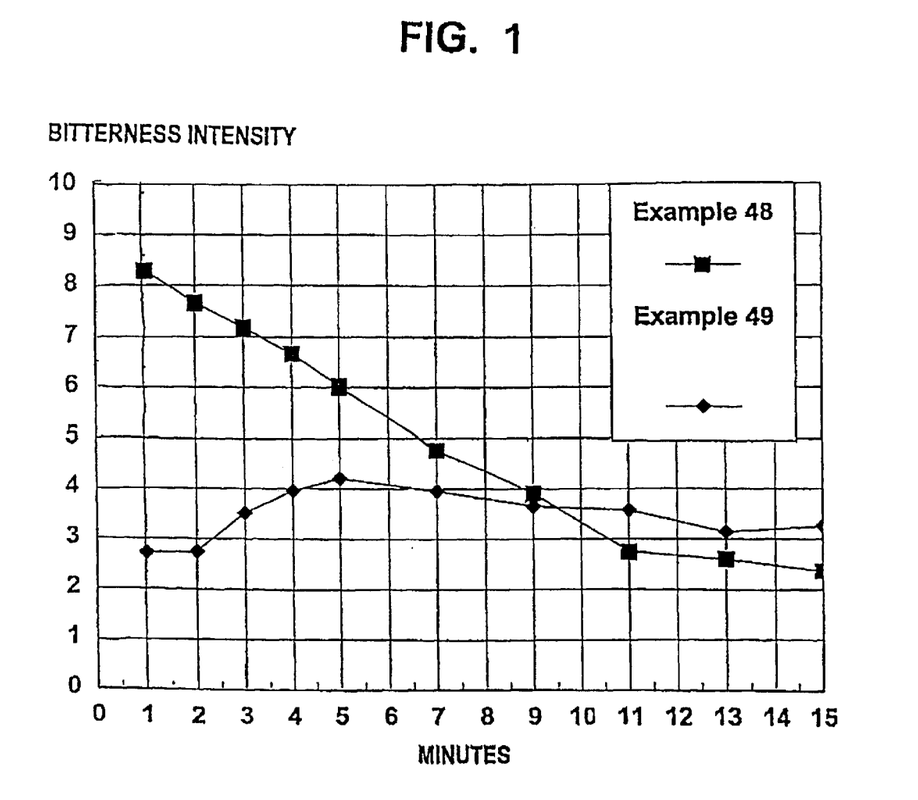
FIG. 1 shows the results of a bitterness time-intensity sensory test for two gum samples with a coating containing caffeine, with one sample containing encapsulated caffeine and the other containing unencapsulated caffeine.

Examples 48 and 49 were sensory tested in a time-intensity test by a nine-member panel using a 10 point scale and judged for bitterness intensity, flavor intensity, and sweetness intensity. Results for bitterness intensity are shown in FIG. 1. Significant difference was found at minutes 1, 2, 3, 4 and 5 for bitterness intensity, but no difference was found for flavor or sweetness intensity.

Using the gum center formulas of Table I, encapsulated ibuprofen can then be used in the coating formula on the various pellet gum formulations. Dosage for 2–5% ibuprofen in coating is 60 to 150 mg per 2–1.5 gram pieces. The following Table 8 shows some sugar and dextrose type formulas:

The above formulations are made by making a syrup by dissolving the sugar and gum talha in solution at about 75% solids at boiling, and suspending titanium dioxide or calcium carbonate in this syrup. Encapsulated ibuprofen and flavor are not mixed with the hot syrup, but added at low levels with one or more coats. After the final coats are applied and dried, wax is applied to give a smooth polish. This process gives a hard shell coating.

A dry charge blend of powdered sugar, dextrose monohydrate or gum talha may be used. When encapsulated ibuprofen is added to the coating, it may be preblended with the dry charge material. The dry charge powder material is applied to the surface after the liquid syrup to help dry the surface before applying another coating. A dry charge may be used to build up a coating, but then finished with a straight syrup to obtain a hard shell. Table 9 gives these types of formulas.

TABLE 9

(DRY WEIGHT PERCENT)

|  | EX. 60 | EX. 61 | EX. 62 | EX. 63 | EX. 64 | EX. 65 |
| --- | --- | --- | --- | --- | --- | --- |
| SUGAR | 72.5 | 79.4 | — | — | 82.5 | — |
| DEXTROSE MONO-HYDRATE | — | — | 75.5 | 84.3 | — | 84.1 |
| POWDERED SUGAR | 20.0* | 15.0* | — | — | — | — |
| POWDER DEXTROSE | — | — | 20.0* | 10.0* | — | — |
| GUM TALHA POWDER | 2.0 | 3.0 | 2.0 | 3.0 | 8.0* | 8.0* |
| GUM TALHA SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| ACTIVE ENCAP-SULATED IBUPROFEN | 5.0 | 2.0 | 2.0 | 2.0 | 5.0 | 3.0 |

*Powder and/or crystalline sugar or gum talha blended with encapsulated ibuprofen may be used.

In Examples 60–63, gum talha is blended in the sugar syrup. In Examples 64 and 65, gum talha powder is dry charged after a gum talha solution is applied in the first stages of coating, then this is followed by a hard shell coating of sugar solution or dextrose solution.

Encapsulated ibuprofen may also be preblended with gum talha solution to form a paste, and to assist in drying when mixed with coating syrup. Preferably this should be done

TABLE 8

(DRY WEIGHT PERCENT)

|  | EX. 50 | EX. 51 | EX. 52 | EX. 53 | EX. 54 | EX. 55 | EX. 56 | EX. 57 | EX. 58 | EX. 59 |
| --- | --- | --- | --- | --- | --- | --- | --- | --- | --- | --- |
| SUGAR | 92.1 | 93.4 | 92.1 | 91.9 | 93.1 | 91.6 |  |  |  |  |
| DEXTROSE MONOHYDRATE |  |  |  |  |  |  | 94.6 | 92.4 | 94.2 | 89.5 |
| GUM TALHA | 2.0 | 3.0 | 4.0 | 2.0 | 3.0 | 4.0 | 1.5 | 3.0 | 1.5 | 3.0 |
| TITANIUM DIOXIDE | 0.5 | 1.0 | 1.0 | — | — | — | 0.5 | 1.0 | — | — |
| CALCIUM CARBONATE | — | — | — | 0.5 | 1.0 | 2.0 | — | — | 1.0 | 2.0 |
| FLAVOR | 0.3 | 0.5 | 0.8 | 0.5 | 0.8 | 0.3 | 0.3 | 0.5 | 0.2 | 0.4 |
| WAX | 0.1 | 0.1 | 0.1 | 0.1 | 0.1 | 0.1 | 0.1 | 0.1 | 0.1 | 0.1 |
| ACTIVE ENCAPSULATED IBUPROFEN | 5.0 | 2.0 | 2.0 | 5.0 | 2.0 | 2.0 | 3.0 | 3.0 | 3.0 | 5.0 | when the encapsulant is water insoluble. The gum talha/encapsulated ibuprofen should also be applied to the coating immediately after being preblended.

Gum talha is especially useful in sugarless coatings with xylitol, sorbitol, maltitol, lactitol, hydrogenated isomaltulose and erythritol. Gum talha acts as a binder, film former and hardener of the coated pellet. The following table gives formulas for a xylitol coating with encapsulated ibuprofen:

TABLE 10

(DRY WEIGHT PERCENT)

| | EX. 66 | EX. 67 | EX. 68 | EX. 69 | EX. 70 | EX. 71 |
|---|---|---|---|---|---|---|
| XYLITOL | 91.8 | 89.4 | 87.7 | 87.1 | 84.9 | 83.8 |
| GUM TALHA | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| ACTIVE ENCAPSULATED IBUPROFEN | 3.0 | 3.0 | 3.0 | 3.0 | 5.0 | 5.0 |

*Lake color dispersed in xylitol solution
**Calcium carbonate used in place of titanium dioxide The above formulas are used to coat pellets by applying a xylitol/gum talha solution in multiple coats and air drying. Color or whitener is also mixed in the solution. After pellets have been coated and dried, talc and wax are added to give a polish.

As in sugar coating, some of the gum talha powder may be blended with powder xylitol for dry charging. Encapsulated ibuprofen may be added with the dry charge material. Also, a gum talha syrup may be made and used as a separate coating with encapsulated ibuprofen and dry charged.

For coating formulas based on sorbitol, maltitol, lactitol, and hydrogenated isomaltulose, gum talha can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. As above, encapsulated ibuprofen can be added with the dry charge. The following formulations may be used.

TABLE 11

(DRY WEIGHT PERCENT)

| | EX. 72 | EX. 73 | EX. 74 | EX. 75 | EX. 76 | EX. 77 |
|---|---|---|---|---|---|---|
| SORBITOL | 91.8 | 88.9 | 84.1 | 83.8 | 73.1 | 66.5 |
| SORBITOL POWDER | 2.0 | 3.0 | 5.0 | 10.0 | 18.0 | 23.0 |
| GUM TALHA | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| ACTIVE ENCAPSULATED IBUPROFEN | 3.0 | 3.0 | 3.0 | 3.0 | 5.0 | 5.0 |

Sorbitol, gum talha, and whitener is blended into a syrup and applied to pellets. After all coating is applied and dried, talc and wax are added to give a polish.

In a similar manner, coatings with maltitol, lactitol, and hydrogenated isomaltulose may be made in the coating formulas in Table 11 by replacing sorbitol with any one of the other polyols and sorbitol powder with the polyol powder. Like sorbitol, the other polyols may become sticky during the coating and drying process, so the dry powder charge with encapsulated ibuprofen may be needed to give the proper drying. In the later stages of the coating process less gum talha could be used and a more pure polyol syrup could be used to give a smooth surface. Also, the dry charge would only be used in the early stages of the coating process. A gum talha syrup may be made and used as a separate coating with encapsulated ibuprofen and dry charged.

In addition to dry charging with the specific polyol, other ingredients may be added to the dry charge to help absorb moisture. These materials could be inert such as talc, calcium carbonate, magnesium carbonate, starches, gums like gum talha or other moisture absorbing materials. Also, powdered sweeteners or flavors could be added with the dry charge.

Some polyols such as sorbitol, maltitol, lactitol, or hydrogenated isomaltulose are not sufficiently sweet compared to sugar or xylitol,-so high intensity sweeteners may be added to the coating such as aspartame, acesulfame K, salts of acesulfame, cyclamate and its salts, saccharin and its salts, alitame, sucralose, thaumatin, monellin, dihydrochalcone, glycyrrhizin, and combinations thereof. If a hot syrup is applied, heat may degrade the sweetener so only stable sweeteners should be used. Generally high intensity sweeteners are added with the polyol/gum talha solution to obtain an even distribution in the coatings.

ENCAPSULATION EXAMPLES

Although a wide variety of medicaments may be encapsulated, encapsulation of caffeine is demonstrated in the next examples. For spray drying, the solids level of an aqueous or alcoholic solution can be about 5–30%, but preferred levels are indicated in the examples listed.

Example A—An 80% shellac, 20% active caffeine powder mixture is obtained by spray drying an alcohol/shellac/caffeine solution at total solids of 10%.

Example B—A 50% shellac, 50% active caffeine powder mixture is obtained by spray drying an appropriate ratio of alcohol/shellac/caffeine solution at 10% solids.

Example C—A 70% Zein, 30% active caffeine powder mixture is obtained by spray drying an alcohol/Zein/caffeine solution at 10% solids.

Example D—A 40% shellac, 60% active caffeine powder mixture is obtained by fluid-bed coating caffeine with an alcohol/shellac solution at 30% solids.

Example E—A 20% Zein, 80% active caffeine powder mixture is obtained by fluid-bed coating caffeine with an alcohol/Zein solution at 30% solids.

Example F—A 40% Zein, 60% active caffeine powder mixture is obtained by fluid-bed coating caffeine with an alcohol/Zein solution at 25% solids.

Example G—An 85% wax, 15% active caffeine powder mixture is obtained by spray chilling a mixture of molten wax and caffeine.

Example H—A 70% wax, 30% active caffeine powder mixture is obtained by spray chilling a mixture of molten wax and caffeine.

Example J—A 70% Zein, 30% active caffeine powder mixture is obtained by spray drying a hot aqueous mixture of caffeine and Zein dispersed in an aqueous, high-pH (pH of 11.6–12.0) media at 10% solids.

Example K—A 20% Zein, 80% active caffeine powder mixture is obtained by fluid-bed coating caffeine with an aqueous, high-pH (pH=11.6–12.0) Zein dispersion of 10% solids.

Example L—A 20% Zein, 20% shellac, 60% active caffeine powder mixture is obtained by spray drying an alcohol/shellac/caffeine mixture and then fluid-bed coating the spray dried product for a second coating of alcohol and Zein.

Examples A to L would all give nearly complete encapsulation and would give reduced bitterness in sugar and sugarless gum formulations. The higher levels of coating would give more reduced bitterness than the lower levels of coating.

Other polymers that are more water soluble and used in coating would give less bitterness of the caffeine in a gum coating.

Example M—An 80% gelatin, 20% active caffeine powder mixture is obtained by spray drying a hot gelatin/caffeine solution at 20% solids.

Example N—A 30% hydroxypropylmethyl cellulose (HPMC), 70% caffeine powder mixture is obtained by fluid-bed coating caffeine with an aqueous solution of HPMC at 10% solids.

Example P—A 50% maltodextrin, 50% active caffeine powder mixture is obtained by spray drying a hot aqueous solution of caffeine and maltodextrin at 30% solids.

Example Q—A 40% gum arabic, 60% active caffeine powder mixture is obtained by fluid-bed coating caffeine with an aqueous solution of gum arabic at 30% solids.

Caffeine could also be used in gum as an agglomerated caffeine to give some reduced bitterness in a gum coating. Agglomerated caffeine can be prepared as in the following examples:

Example R—A 15% hydroxypropylmethyl cellulose (HPMC), 85% active caffeine powder mixture is prepared by agglomerating caffeine and HPMC blended together, with water being added, and the resulting product being dried and ground.

Example S—A 15% gelatin, 85% active caffeine powder mixture is made by agglomerating caffeine and gelatin blended together, with water being added, and the resulting product being dried and ground.

Example T—A 10% Zein, 90% active caffeine powder mixture is made by agglomerating caffeine with an alcohol solution containing 25% Zein, and drying and grinding the resulting product.

Example V—A 15% shellac, 85% active caffeine powder mixture is made by agglomerating caffeine with an alcohol solution containing 25% shellac, and drying and grinding the resulting product.

Example W—A 20% HPMC, 80% active caffeine powder mixture is obtained by agglomerating an HPMC and caffeine mixture blended together, with water being added, and the resulting product being dried and ground.

Example X—A 20% Zein, 80% active caffeine powder mixture is obtained by agglomerating caffeine and Zein dissolved in high-pH water (11.6–12.0) at 15% solids, with the resulting product being dried and ground.

Example Y—A 20% wax, 80% active caffeine powder mixture is obtained by agglomerating caffeine and molten wax, and cooling and grinding the resulting product.

Example Z—A 15% maltodextrin, 85% active caffeine powder mixture is obtained by agglomerating a blend of caffeine and maltodextrin, then adding water, drying and grinding.

Multiple step agglomeration/encapsulation procedures can also be used in making release-modified caffeine for use in the formulations in previous tables. Examples of multiple step treatments are here described:

Example AA—Caffeine is spray dried with maltodextrin at 30% solids to prepare a powder. This powder is then agglomerated with a hydroxypropylmethyl cellulose (HPMC) in a ratio of 85/15 powder/HPMC, wetted with water and dried. After grinding the resulting powder will contain about 68% active caffeine, 17% maltodextrin and 15% HPMC.

Example BB—Caffeine is agglomerated with HPMC in a ratio of 85/15 caffeine/HPMC. After drying and grinding, the resulting powder is fluid-bed coated with an alcohol/shellac solution at about 25% solids to give a final product containing about 60% active caffeine, 10% HPMC, and about 30% shellac.

Example CC—Caffeine is agglomerated with HPMC in a ratio of 85/15 caffeine/HPMC. After drying and grinding, the resulting powder is agglomerated with a 15% solids, high-pH, aqueous solution of Zein to give a final product containing about 60% active caffeine, 10% HPMC, and 30% Zein.

Example DD—Caffeine is spray dried with a 25% solution of gelatin.

The spray dried product is then agglomerated with a 15% solids, high-pH, aqueous solution of Zein. The final product will contain about 50% active caffeine, 20% gelatin, and 30% Zein.

Example EE—Caffeine is agglomerated with molten wax in a ratio of 85/15 caffeine/wax. When the mixture cools and is ground, it is fluid-bed coated with a 25% Zein—75% alcohol solution, giving a final product containing 60% active caffeine, 10% wax and 30% Zein.

These examples, when used in any of the formulations noted in previous tables, give caffeine a reduced bitterness. These multiple step procedures can actually give more reduced bitterness than the single step processes. Multiple step processes of more than two steps may give even more reduced bitterness, but may generally become less cost effective and less efficient. Preferably, spray drying can be the first step with additional steps of fluid-bed coating, spray chilling and agglomeration being part of the latter steps.

For absorption type examples, the reduced bitterness of caffeine is dependent on the type of absorbing material. Most materials like silicas, silicates, cellulose, carbonates, and hydroxides would be expected to give a more reduced bitterness than amorphous sugar and sugar alcohols. Some examples:

Example FF—A hot 10% solution of caffeine is sprayed onto a precipitated silica to absorb the caffeine. The mixture is ground and the final product is about 50% active caffeine.

Example GG—A hot 10% solution of caffeine is sprayed onto a pharmasorb clay. The mixture is dried and ground and gives a final product of about 80% clay and 20% active caffeine.

Example HH—A 10% solution of caffeine is sprayed onto a microcrystalline cellulose powder. The mixture is dried and ground and gives a product that is about 70% microcrystalline cellulose and 30% active caffeine.

The caffeine can also be used with a variety of high-intensity sweeteners and blended together before encapsulation, agglomeration, absorption, and entrapment. This can further reduce bitterness associated with caffeine. Some examples are:

Example JJ—Caffeine and aspartame are blended together in a 2/1 ratio as a powder. This mixture is then spray chilled with wax in a ratio of 60/40 mixture/wax to obtain a powder containing 40% caffeine, 20% aspartame, and 40% wax.

Example KK—Caffeine and thaumatin in a 4/1 ratio are dissolved in water with a 10% solution of gelatin and spray dried. This spray dried powder is then agglomerated with a high-pH aqueous 15% Zein solution. The mixture is dried and ground and gives a product containing 40% caffeine, 10% thaumatin, 35% gelatin, and 15% Zein.

Example LL—Caffeine and alitame in a 7/1 ratio are prepared in a hot 10% solution. This solution is sprayed onto a high absorption silica powder. The mixture is dried, ground and fluid-bed coated with an alcohol/shellac mixture, giving a product that contains 35% caffeine, 5% alitame, 40% silica, and 20% shellac.

Example MM—Caffeine and sodium cyclamate in a 1/1 ratio are blended together as a powder and then agglomerated with water and hydroxypropylmethyl cellulose (HPMC). This blend is dried, ground and agglomerated further with a high-pH, aqueous 15% solution of Zein to obtain a product containing 34% sodium cyclamate, 34% caffeine, 12% HPMC and 20% Zein.

Example NN—Caffeine and glycyrrhizin in a 1/1 ratio are blended together as a powder and fluid-bed coated with a solution of 25% shellac in alcohol. The coated product is agglomerated further with water and hydroxypropylmethyl cellulose (HPMC) to obtain a product containing 30% caffeine, 30% glycyrrhizin, 25% shellac, and 15% HPMC.

Example PP—Caffeine and sodium saccharin in a ratio of 1/1 are blended together as a powder and fluid bed coated with a solution of 25% shellac in alcohol. The coated product is agglomerated further with water and hydroxypropylmethyl cellulose (HPMC) to obtain a product containing 30% caffeine, 30% sodium saccharin, 25% shellac, and 15% HPMC.

If the blends of caffeine and other high-intensity sweeteners of above examples are added to gum coatings, a significant reduced caffeine bitterness would be expected. This would improve the quality of flavor. The following are examples of fiber extruded PVAC/caffeine blends to give a delayed release of caffeine and give reduced bitterness:

Example QQ—Medium molecular weight PVAC and caffeine at a ratio of 3/1 are blended together as a powder and extruded. The fibers are cooled and ground to give a product containing 75% PVAC and 25% caffeine.

Example RR—Medium molecular weight PVAC, caffeine and aspartame at a ratio of 12/4/1 are blended together as a powder and extruded, the resulting fibers are ground and give a product containing 70% PVAC, 24% caffeine and 6% aspartame.

Example SS—Medium molecular weight PVAC, caffeine, aspartame, and sodium gluconate at a ratio of 16/4/4/1 are blended together as a powder and extruded. The fibers are ground and gives a product containing 64% PVAC, 16% caffeine, 16% sodium gluconate, and 4% aspartame.

Sodium gluconate is a bitterness inhibitor that can be mixed with caffeine before being encapsulated or entrapped. This bitterness inhibitor, along with other bitterness inhibitors such as sodium salts of chloride, ascorbic acid, glutamic acid and citric acid, as well as other various organic compounds, can be added to caffeine to reduce bitterness.

Example TT—A 20% hot aqueous solution of maltodextrin is mixed with a 40% hot solution of sodium gluconate. Two liters of this mixture is combined with 100 grams of caffeine, dispersed and spray dried. A final product containing 50% maltodextrin, 33% sodium gluconate and 17% caffeine is obtained.

Example VV—A 2400 ml quantity of a 25% hot aqueous solution of maltodextrin is mixed with 50 grams of aspartame to form a suspension.

To this is added a hot aqueous solution of 400 grams of sodium gluconate, 200 grams of caffeine, 1200 grams of hot water. This mixture is spray dried to obtain a powder containing 48% maltodextrin, 32% sodium gluconate, 16% caffeine and 4% aspartame.

Example WW—To a 2400 gram quantity of a 25% hot solution of maltodextrin, 200 grams of citric acid and 50 grams of aspartame are added and suspended. To this mixture is added a hot aqueous solution of 400 grams of sodium gluconate, 200 grams of caffeine and 1200 grams of hot water. This mixture is spray dried to obtain a powder containing 41% maltodextrin, 28% sodium gluconate, 14% caffeine, 14% citric acid and 3% aspartame.

It should be appreciated that the methods and compositions of the present invention are capable of being incorporated in the form of a variety of embodiments, only a few of which have been illustrated and described above. The invention may be embodied in other forms without departing from its spirit or essential characteristics. It will be appreciated that the addition of some other ingredients, process steps, materials or components not specifically included will have an adverse impact on the present invention. The best mode of the invention may therefore exclude ingredients, process steps, materials or components other than those listed above for inclusion or use in the invention. However, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. A method of producing a coated chewing gum product containing a physically-modified active agent in order to modify the release of the active agent in the mouth of an individual comprising the steps of:

a) mixing a quantity of the active agent, which comprises a compound that has a desired therapeutic or physiological effect, with a modifying agent to produce a physically-modified active agent; and then b) applying the physically-modified active agent and other coating ingredients to a chewing gum core to form the coated chewing gum product wherein the coating includes a quantity of the physically-modified active agent to provide an active agent level in the coated chewing gum product of from about 50 micrograms to about 500 milligrams.

2. The method of claim 1 wherein said modifying agent is an encapsulating agent.

3. The method of claim 2 wherein the active agent and encapsulating agent are also mixed with a solvent and the resulting mixture is dried prior to being added to the chewing gum coating.

4. The method of claim 3 wherein the encapsulating material is selected from the group consisting of maltodextrin, gum arabic, Zein and shellac.

5. The method of claim 3 wherein the mixture is spray dried and the solvent is selected from the group consisting of alcohol and water.

6. The method in claim 3 wherein a high-potency sweetener selected from the group consisting of aspartame, alitame, salts of acesulfame, cyclamate and its salts, saccharin and its salts, thaumatin, monellin, dihydrochalcones and combinations thereof is mixed in the mixture in combination with the active agent.

7. A chewing gum made according to the method of claim 3.

8. The method according to claim 2 wherein the active agent is fluid-bed coated with a solution of encapsulating agent and solvent in order to modify the release of active agent in the chewing gum coating.

9. The method of claim 8 wherein the solvent is selected from the group consisting of alcohol and water.

10. The method of claim 8 wherein the encapsulating material is selected from the group consisting of shellac and Zein.

11. The method of claim 8 wherein an additional high-potency sweetener selected from the group consisting of aspartame, alitame, salts of acesulfame, cyclamate and its salts, saccharin and its salts, thaumatin, monellin, dihydrochalcones and combinations thereof is mixed in the mixture in combination with the active agent.

12. A chewing gum made according to the method of claim 8.

13. The method according to claim 2 wherein the active agent is encapsulated by coacervation in order to modify the release of active agent in the chewing gum coating.

14. The method of claim 2 wherein the active agent is mixed with a molten encapsulating agent and the active agent is encapsulated by spray chilling in order to modify the release of active agent in the chewing gum coating.

15. The method of claim 14 wherein the encapsulating agent comprises wax.

16. The method of claim 2 wherein the active agent is mixed with a polymer as the encapsulating agent and the resulting mixture is extruded into fine fibers in such a way as to encapsulate the active agent in order to modify the release of the active agent in the chewing gum coating.

17. The method of claim 16 wherein the polymer is selected from the group consisting of PVAC, hydroxypropyl cellulose, polyethylene and plastic polymers.

18. The method of claim 1 wherein the active agent is mixed with an absorbent as the modifying agent.

19. The method of claim 1 wherein said active agent is selected from the group consisting of vitamins, analgesics, antacids, antihistamines, decongestants, anesthetics and stimulants.

20. The method of claim 19 wherein said analgesics are selected from the group consisting of aspirin, acetaminophen, ketoprofen, naproxen, and ibuprofen.

21. The method of claim 19 wherein said antacids are selected from the group consisting of cimetidine, ranitidine, omeprazole and famotidine.

22. The method of claim 19 wherein said antihistamines are selected from the group consisting of cimetidine, ranitidine famotidine and chlorpheniramine.

23. The method of claim 19 wherein said decongestants are selected from the group consisting of dextromethorphan, noscapine, and pseudoephedrine.

24. The method of claim 19 wherein said stimulant is caffeine.

25. The method of claim 1 wherein said active agent is nicotine or a nicotine substitute.

26. The method of claim 1 wherein the active agent is caffeine and the caffeine comprises between about 0.2% and about 5% of the coated chewing gum product.

27. A method of producing a coated chewing gum product containing a physically-modified active agent in order to modify the release of the active agent comprising the steps of:
   a) mixing a quantity of the active agent, which comprises a compound that has a desired therapeutic or physiological effect, with an agglomerating agent and a solvent to partially coat the active agent;
   b) removing the solvent from the mixture of active agent and agglomerating agent to form a dried material; and then
   c) applying the dried material and other coating ingredients to a chewing gum core to form the coated chewing gum product wherein the coating includes a quantity of the dried material to provide an active agent level in the coated chewing gum product of from about 50 micrograms to about 500 milligrams.

28. The method of claim 27 wherein the level of coating of the agglomerated active agent is at least about 5%.

29. The method of claim 27 wherein the level of coating of the agglomerated active agent is at least about 15%.

30. The method of claim 27 wherein the level of coating of the agglomerated active agent is at least about 20%.

31. The method of claim 27 wherein the dried material is ground to a powder prior to adding the dried material to the chewing gum.

32. The method of claim 27 wherein an active agent which has not been treated with a modifying agent is also added to the chewing gum coating.

33. The method of claim 22 wherein the active agent is caffeine and the caffeine comprises between about 0.2% and about 5% of the coated chewing gum product.

34. A method of producing a coated chewing gum product containing a physically-modified active agent in order to delay the release of the active agent in the mouth of an individual comprising the steps of:
   a) mixing a quantity of the active agent, which comprises a compound that has a desired therapeutic or physiological effect, with a water-insoluble modifying agent to produce a physically-modified active agent; and then
   b) applying the physically-modified active agent and other coating ingredients to a chewing gum core to form the coated chewing gum product wherein the coating includes a quantity of the physically-modified active agent to provide an active agent level in the coated chewing gum product of from about 50 micrograms to about 500 milligrams.

* * * * *